(12) United States Patent
Mangino

(10) Patent No.: US 10,300,029 B2
(45) Date of Patent: *May 28, 2019

(54) ORGAN PROTECTION SOLUTIONS AND METHOD OF USE

(71) Applicant: VIRGINIA COMMONWEALTH UNIVERSITY, Richmond, VA (US)

(72) Inventor: Martin Mangino, Powhatan, VA (US)

(73) Assignee: Virginia Commonwealth University, Richmond, VA (US)

( * ) Notice: Subject to any disclaimer, the term of this patent is extended or adjusted under 35 U.S.C. 154(b) by 27 days.

This patent is subject to a terminal disclaimer.

(21) Appl. No.: 15/293,689

(22) Filed: Oct. 14, 2016

(65) Prior Publication Data

US 2017/0151198 A1    Jun. 1, 2017

Related U.S. Application Data

(63) Continuation-in-part of application No. PCT/US2015/025544, filed on Apr. 13, 2015, which is a continuation of application No. 14/253,982, filed on Apr. 16, 2014, now Pat. No. 9,399,027, which is a continuation-in-part of application No. 13/589,441, filed on Aug. 20, 2012, now Pat. No. 8,753,806.

(60) Provisional application No. 62/050,468, filed on Sep. 15, 2014, provisional application No. 61/532,153, filed on Sep. 8, 2011.

(51) Int. Cl.
*A61K 31/191* (2006.01)
*A01N 1/00* (2006.01)
*A61K 31/08* (2006.01)
*A01N 1/02* (2006.01)

(52) U.S. Cl.
CPC .......... *A61K 31/191* (2013.01); *A01N 1/0221* (2013.01); *A61K 31/08* (2013.01)

(58) Field of Classification Search
CPC ..... A61K 31/191; A61K 31/08; A01N 1/0221
See application file for complete search history.

(56) References Cited

U.S. PATENT DOCUMENTS

| | | | | |
|---|---|---|---|---|
| 8,067,150 B2* | 11/2011 | Mangino | ........................ | 435/1.1 |
| 8,753,806 B2* | 6/2014 | Mangino | ........................ | 435/1.2 |
| 9,399,027 B2* | 7/2016 | Mangino | .............. | A61K 31/191 |
| 2014/0228436 A1* | 8/2014 | Mangino | .............. | A61K 31/191 |

* cited by examiner

*Primary Examiner* — Satyendra K Singh
(74) *Attorney, Agent, or Firm* — W&C IP

(57) ABSTRACT

An organ protectant solution which is intravenously administered includes at least one oncotic agent and optionally a high concentration of cell-impermeant molecules. Together, they promote transfer of water from cells to interstitium and into the capillaries, thereby preventing or reducing cell swelling, maintaining blood circulation and oxygenation of tissues, and extending the "Golden Hour" for traumatic and/or hemorrhagic shock patients. In addition, compositions comprising PEG-20k and methods of their use for preserving and/or reanimating harvested organs ex vivo for lengthy periods of time (e.g. at least about 8-24 hours) are also provided.

8 Claims, 20 Drawing Sheets

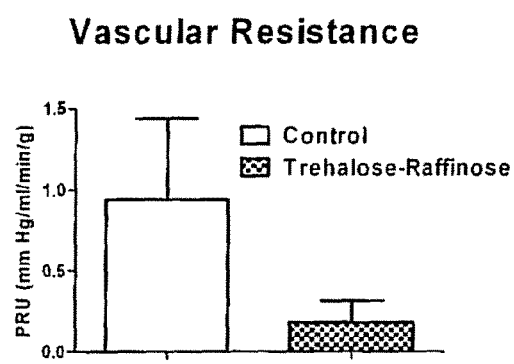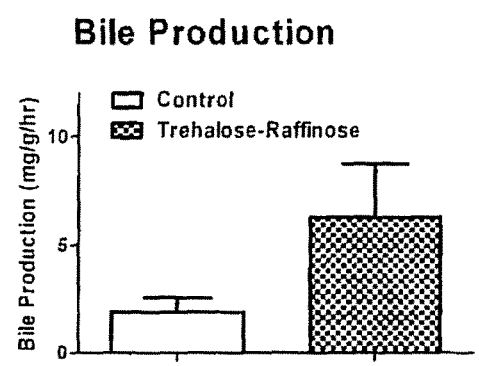
Figure 3AFigure 3B

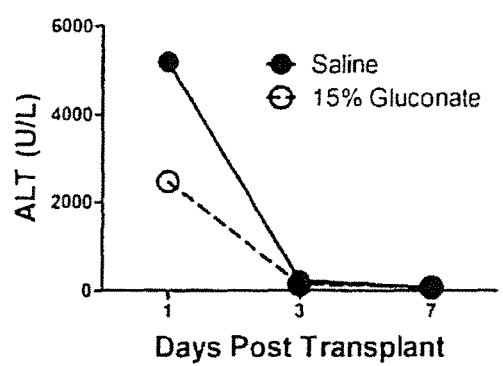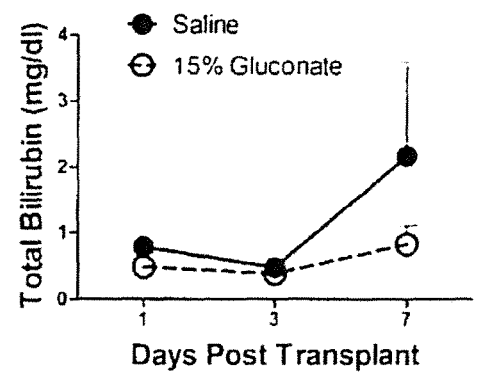
Figure 9A                                    Figure 9B

ORGAN PROTECTION SOLUTIONS AND METHOD OF USE

CROSS-REFERENCE TO RELATED APPLICATIONS

This application is a continuation-in-part of International patent application PCT/US2015/025544 filed Apr. 13, 2015, which claims priority to U.S. patent application Ser. No. 14/253,982 filed Apr. 16, 2014 and U.S. Provisional Patent Application 62/050,468 filed on Sep. 15, 2014. The continuation-in-part U.S. patent application Ser. No. 14/253,982 claims priority to U.S. Provisional Patent Application 61/532,153 filed on Sep. 8, 2011, and U.S. patent application Ser. No. 13/589,441, filed Sep. 20, 2012. The complete contents thereof are herein incorporated by reference.

STATEMENT OF GOVERNMENT INTEREST

This invention was made with government support under W81XWH1210599 awarded by the Department of Defense. The government has certain rights in the invention.

BACKGROUND

Field of the Invention

The invention is directed to composition and in vivo and ex vivo methods for organ protection. In particular, some of the compositions and methods are used in vivo to treat or prevent ischemic injury to organs, and some of the compositions and methods are used ex vivo to treat or prevent damage to harvested organs.

Prior Art

Deaths due to injury in the US reached over 190,000 and costs over $400 billion a year in health care costs and lost productivity in 2012[1]. Deaths from trauma are the number 1 cause of death for people under 44 years of age in the US and the third leading cause of death overall for all age groups. Trauma accounts for about 30% of all life years lost in the US, compared to cancer (16%), heart disease (12%), and HIV (2%)[2]. For all traumatic injuries, hemorrhagic shock is responsible for over 35% of pre-hospital deaths and over 40% of all deaths within the first 24 hours. This is second only to trauma deaths induced by severe CNS injury[3]. Finally, hemorrhagic hypotension exposes the patient to immediate complications of life threatening infections, coagulopathies, and multiple organ failure[4,5].

Initial therapy of trauma and hemorrhage shock centers on effective cessation of bleeding and on the infusion of large volumes (2 to 8 liters) to replace lost blood volume. This is considered necessary to restore normal circulatory functions such as arterial blood pressure, cardiac output, oxygen consumption and renal function. Conventionally, isotonic fluids are used for high volume resuscitation. Many cellular complications and practical limitations have been cited while using high volume fluids for resuscitation. When blood is lost, the greatest immediate need is to stop further blood loss, but the second greatest need is replacing the lost volume. If the fluid volume is maintained, remaining red blood cells may still be sufficient to circulate and oxygenate body tissues for a period of time. In this scenario, it may be possible to reduce or prevent ischemic injury if appropriate medical or surgical intervention can be accomplished.

Recently, resuscitation of hemorrhaged animals and injured patients has been performed with low volume hyper-osmotic saline solutions with little success. Glucose or mannitol has been tested with less successful results. Small volume resuscitation has been successfully used in some cases using hyperoncotic albumins or high molecular weight tense state polymerized hemoglobins. The use of hypertonic saline solutions (HTS) or colloid solutions (albumin, HES, Hetastarch, Hextend) have had very limited success in clinical trauma and resuscitation, and, due to their mechanism of action, they do not prevent cell swelling. Crystalloids are available for pre-hospital use because they can be safely transported and stored but they are generally limited in their effectiveness. Attempts to modify basic intravenous crystalloids for pre-hospital resuscitation by adding hypertonic NaCl or starch (Hextend) as a volume expander have had disappointing results[6,7]. The future use of effective spray dried blood products will be a valuable tool in pre-hospital settings since they replace chemical coagulation precursors and factors. The use of fresh frozen plasma in the field, which is currently being tested at many centers, will also be useful but it too is limited by the need for refrigeration[8].

However, none of these procedures is known to be effective in preventing lethal cell swelling in vivo. Cells, organs, and tissues that suffer from lack of oxygen delivery, as occurs during traumatic shock and hemorrhagic hypovolemia, begin to swell with water because they lose energy dependent volume control mechanisms. In patients suffering from acute hemorrhagic shock and/or trauma, there is substantial intracellular oxygen deprivation, which in turn drops ATP concentration. Due to lack of ATP, the cellular sodium pump fails and free sodium enters the cell, followed by osmotic water movement. Movement of water into the cell causes swelling that leads to organ failure and death. Massive cell swelling further compresses the capillaries and sinusoids and impedes microcirculatory flow through organs and tissues even when the blood pressure is restored after hemorrhage. This is called the "no reflow phenomenon" and it occurs largely from local cell swelling.

This is particularly a problem in battlefield or civilian pre-hospital settings where large volumes cannot be carried and administered to patients in need of rapid paramedical intervention and transport to hospital or surgical treatment centers. There is a so-called "golden hour" of time during which restoration of blood volume and prevention of ischemic injury must be achieved to prevent catastrophic organ failure and death. There is no present day technology to deal with cell swelling and tissue damage to patients experiencing prolonged periods of shock and low volume resuscitation.

In addition, the treatment of choice for patients in end-stage heart failure is heart transplantation. Donor heart availability limits the use of this procedure and has given birth to new mechanical assist or replacement devices that are generally intended to bridge patients to heart transplantation by allowing them to survive on longer wait lists. While this approach works, the availability of more hearts would be welcome. These new hearts would likely enter the donor pool by expanding the current donor criteria and accepting hearts that are injured from warm ischemia (donation after cardiac death, DCD). However, these hearts are currently considered to be unusable and need to be reconditioned to improve function (reanimated) before they can be considered acceptable as transplantable donor organs.

Mechanisms of reanimation have focused on repair and replacement of severely damaged mitochondria in cardiomyocytes from DCD hearts because mitochondrial death is the most likely causative event in DCD heart dysfunction, based on preliminary data in human DCD heart recovery. A prolonged ex-vivo perfusion period between donor heart recovery and transplantation is required to affect mitochondrial repair or replacement through biogenesis. It may be possible to affect mitochondrial biogenesis (replacement) provided the reanimation period is long enough and provided the heart's metabolic needs can be maintained during that period. During this repair period, the myocardium must be adequately perfused. Currently, this is not possible because stable perfusion of the myocardium ex-vivo with existing perfusion preservation solutions (MPS) do not work. Typically, tissue edema and metabolic cell swelling occur early in heart perfusion, which limits adequate tissue oxygen delivery over the prolonged times that are needed for repair.

There is a need for improved compositions and methods to lengthen the time available between organ donation and transplantation, and also to permit time for compromised organs to regain functionality prior to transplant.

SUMMARY

Embodiments of the invention provide an organ protectant solution comprising non-toxic cell impermeants and oncotic agents and methods for administering it to trauma patients early in pre-hospital settings. The cell-impermeant molecule may also act as an oncotic agent. The solutions act to favorably readjust the biophysical forces around the ischemic cells and tissues to promote water movement out of the cells and prevent or reverse lethal ischemic cell swelling. Cell-impermeant molecules in the solution load the interstitial space and establish an osmotic gradient from cell to interstitium. Oncotic agents in the solution are restricted to the intravascular space and establish an osmotic or oncotic gradient from interstitium to capillary space to further draw water from the interstitial space into the capillaries and ultimately out of the tissue. The osmotic gradient established by the concomitant use of both impermeants and oncotic agents provides salutatory effects for an individual in need thereof. Water movement into the capillary by the oncotic action of the invention is convectively washed away from the tissue by local blood flow, especially in the microcirculation of capillaries where gas exchange occurs. This potentiates and amplifies the effects of the impermeants alone by convective solvent transfer of the water out of the organ and tissues. Furthermore, movement of interstitial water into the capillary space increases the capillary hydrostatic pressure and provides for more local blood flow and oxygen delivery to the tissues, which reverses the primary low flow problem.

Another embodiment of the invention is an organ protectant solution of cell-impermeants that reduces the cell swelling that underlies ischemic injury. Prevention of lethal cell swelling in vivo will increase the survivability in hemorrhagic shock and trauma patients. The organ protection solution comprises one or more cell impermeants (specific anions and small saccharides) in low volume resuscitation solutions, which are easily administered in the field and can improve resuscitation outcome. The organ protection solution protects organs during severe shock and severe hypotension (acute drop of blood pressure) and/or rapid blood loss due to traumatic injury. Cell swelling can produce lethal injury under any of these conditions and the organ protection solutions described herein target the cell swelling mechanism to make the cells more resistant to damage during low flow states.

Another embodiment of the invention provides an organ protectant solution comprising oncotic agents. An organ protectant solution containing oncotic molecules provides the benefit of oncotic pressure within the intravascular spaces. Oncotic pressure within the capillaries promotes transfer of water from the interstitial space into the capillary space and channels cell water away by convective flow movement (blood flow). This action provides the additional benefit of adding fluid to the intravascular space, increasing perfusion pressure and further contributing to maintaining fluid volume and flow in the circulatory system, thereby moving the remaining red blood cells through tissues to oxygenate cells and back to the lungs for $CO_2/O_2$ gas exchange.

Some embodiments of the invention provide a method for prolonging low volume resuscitation in a subject in need thereof, comprising the steps of
administering intravenously or intraosseosly to said subject 2000 milliliters or less of
an organ protectant solution comprising
one or more oncotic agents present at a concentration of at least 1-30% by weight and with a molecular weight and size sufficient to restrict said one or more oncotic agents to a vascular space in said subject, wherein said one or more oncotic agents increase oncotic pressure and cause water to transfer from said interstitial space into said vascular space; and
reducing cell swelling and promoting microcirculatory blood flow for at least 2 hours in said subject.

In some embodiments, the organ protectant solution further comprises one or more cell impermeant molecules present at a concentration of at least 10-60% by weight, wherein at least one of said one or more cell impermeant molecules can cross a capillary endothelium and preferentially load into an extracellular fluid compartment in said subject and increase a theoretical extracellular fluid osmolarity without entering one or more of endothelial and parenchymal cells.

In some embodiments, the organ protectant solution comprises a molecule or molecules (e.g., 10-30% by volume) that possess hybrid characteristics whereby some of the active solute material is able to leave the capillary space to load into the interstitium to act as a cell impermeant while the remainder of the material stays in the capillary space to act as an oncotic agent. These hybrid molecules are characterized by their intermediate (hybrid) oncotic reflection coefficients ($\sigma_d$) in most vascular beds of 0.3-0.7. Some polymers of PEG (e.g. PEG-20k, PEG having weights in excess of 20kDa, etc.) possess these biophysical characteristics.

In some embodiments, the organ protectant solution contains a pure oncotic agent where most or all of the material stays in the capillary and a cell impermeant molecule such as gluconate, raffinose, trehalose, etc. In other embodiments, the organ protectant solution contains a hybrid impermeant molecule (e.g. PEG-20k) that both stays in the capillary space to act as an oncotic agent and escapes the capillary to act as an impermeant molecule.

In some embodiments, at least one of said one or more oncotic agents is polyethylene glycol polymers (PEG) with a molecular weight of at least 4,000. The PEG may be at a concentration of 5% to 30% by weight in the composition. In some aspects, the PEG is PEG-20,000 and in other aspects, the PEG is PEG-35,000.

In some aspects of the invention, the cell impermeant molecule is selected from the group consisting of sorbitol, gluconate, trehalose, raffinose, lactobionate, and maltitol.

Some embodiments of the invention provide a method of treating severe hypotension in a subject comprising the step of administering intravenously or intraosseosly a pharmaceutically acceptable organ protectant solution, comprising at least one PEG polymer with a molecular weight of at least 20,000 at a concentration of 5% to 30% by weight, in an amount sufficient to raise blood pressure to at least 55 mmHg in said subject and extend a time period for safe low volume resuscitation to at least 2 hours.

In some embodiments, the organ protectant solution further comprises one or more cell impermeant molecules present at a concentration of at least 10-60% by weight, wherein at least one of said one or more cell impermeant molecules can cross a capillary endothelium and preferentially load into an extracellular fluid compartment in said subject and increase a theoretical extracellular fluid osmolarity without entering one or more of endothelial and parenchymal cells.

Some embodiments of the invention provide an organ protectant solution, wherein one or more of gluconate, raffinose, and trehalose at 10-35% by weight, and one or more polyethylene glycol polymers (PEG) with a molecular weight of 4,000-35,000 at a concentration of 1-30% by weight, and a pharmaceutically acceptable carrier are present in one or more infusion(s) of no more than 2000 ml per infusion. In some embodiments, the one or more infusion(s) has a volume of no more than 500 ml. In some embodiments, the PEG is PEG-20,000 at a concentration of 10-20%. In other embodiments, the PEG is PEG-35,000 at a concentration of 20-30%.

Some embodiments of the invention provide an infusion bag containing one or more polyethylene glycol polymers (PEG) with a molecular weight of 4,000-35,000 at a concentration of 1-30% by weight, and a pharmaceutically acceptable carrier in a volume of no more than 2000 ml.

Additional embodiments of the invention provide a method for protecting organs for transplantation, comprising the steps of administering to a Donation after Cardiac Death (DCD) organ donor or a Donation after Brain Death (DBD) organ donor an organ protectant solution comprising at least one of one or more oncotic agents present at a concentration of at least 1-20% by weight and with a molecular weight and size sufficient to restrict said one or more oncotic agents to a vascular space in said subject, wherein said one or more oncotic agents increase oncotic pressure and cause water to transfer from said interstitial space into said vascular space; and maintaining circulation of said DCD or DBD organ donor for a suitable period of time (e.g. 1-36 hours), and removing surgically said organs of said DCD or DBD organ donor, and flushing said organs for cold storage or perfusion prior to said transplantation.

In some embodiments, the organ protectant solution is provided as a single use IV infusion solution. The container for an IV infusion solution is typically a lightweight, flexible plastic bag. The amount of solution in the container will typically be less than 2000 ml, and is preferably less than 1000 ml, or more preferably 100-500 ml. When administered to a patient, approximately 100-2000 ml of an organ protectant solution is administered intravenously as quickly as possible when the condition or suspected condition of shock is diagnosed, or after the start of an ischemic event or to protect tissues from a potential ischemic event.

Additional aspects of the invention provide compositions and methods of using the compositions to preserve and/or restore organ function ex vivo during the period of time between harvesting an organ from a donor and transplanting the organ into a recipient.

It is an object of the invention to provide an aqueous liquid composition for preserving and/or reanimating a harvested organ ex vivo, comprising i) a hybrid molecule that is both an oncotic agent and a cell impermeant, or a combination of molecules, at least one of which is an oncotic agent and at least one of which is a cell impermeant; ii) one or more sugars; iii) one or more buffering agents; iv) one or more mineral sources; v) one or more agents that activate ATP synthesis; and vi) an antioxidant. In further aspects, the aqueous liquid composition also includes hemoglobin or a synthetic hemoglobin. In some aspects, the hybrid molecule is a polyethylene glycol (PEG) polymer. In further aspects, the PEG polymer is PEG-20k. In yet further aspects, the combination of molecules includes albumin and gluconate. In some aspects, the one or more sugars includes glucose or gluconate. In other aspects, the one or more buffering agents includes HEPES. In additional aspects, the one or more mineral sources includes a source or one or more of magnesium, calcium, sodium, and potassium. In yet further aspects, the solution includes one or more agents that decrease xanthine oxidase activity, such as allopurinol. In other aspects, the aqueous liquid composition further comprises one or more high temperature adaptation agents. In further aspects, the one or more high temperature adaptation agents is octanoate or allopurinol. In further aspects, the aqueous liquid composition comprises

| | |
|---|---|
| PEG-20K | 2.5% (w/v), |
| KH$_2$PO$_4$ | 15 mM, |
| adenosine | 5 mM, |
| glucose | 10 mM, |
| Na-Octanoate | 1 mM, |
| HEPES | 12 mM, |
| Mg-Gluconate | 5 mM, |
| Na-Gluconate | 92 mM, |
| CaCl$_2$ dihydrate | 0.5 mM, |
| allopurinol | 1 mM, and |
| glutathione (reduced) | 3 mM. |

The invention also provides an ex vivo method of preserving or reanimating a harvested organ, comprising perfusing the harvested organ with an aqueous liquid composition comprising a hybrid molecule that is both an oncotic agent and a cell impermeant, or a combination of molecules, at least one of which is an oncotic agent and at least one of which is a cell impermeant; one or more sugars; one or more buffering agents; one or more mineral sources; and one or more agents that activate ATP synthesis, and an antioxidant. In some aspects, the aqueous liquid composition comprises

| | |
|---|---|
| PEG-20K | 2.5% (w/v), |
| KH$_2$PO$_4$ | 15 mM, |
| adenosine | 5 mM, |
| glucose | 10 mM, |
| Na-Octanoate | 1 mM, |
| HEPES | 12 mM, |
| Mg-Gluconate | 5 mM, |
| Na-Gluconate | 92 mM, |
| CaCl$_2$ dihydrate | 0.5 mM, |
| allopurinol | 1 mM, and |
| glutathione (reduced) | 3 mM. |

In additional aspects, the step of perfusing is performed at a temperature ranging from 15 to 21° C., inclusive. In yet further aspects, the step of perfusing takes place for a period of at least 1, 2, 3, 4, 5, 6, 7, 8, 9, 10, 11, 12, 13, 14, 15, 16, 17, 18, 19, 20, 21, 22, 23 or 24 hours.

BRIEF DESCRIPTION OF THE DRAWINGS

FIG. 3A-B. A) Bar graph illustrating measurements for vascular resistance in a donation after cardiac death (DCD) model for liver donation. B) Bar graph illustrating measurements for bile reduction in a DCD model for liver donation.

FIG. 9A-B. A) Line graph showing enzyme release (liver injury) after liver transplantation in control (saline) and impermeant treated (15% gluconate) donors before donation after cardiac death (DCD). B) Line graph showing total bilirubin levels after liver transplantation in control (saline) and impermeant treated (15% gluconate) donors before donation after cardiac death (DCD). Rising bilirubin is an indicator of the development of ischemic cholangiopathy in DCD liver transplant recipients.

DETAILED DESCRIPTION

Figure 1A:
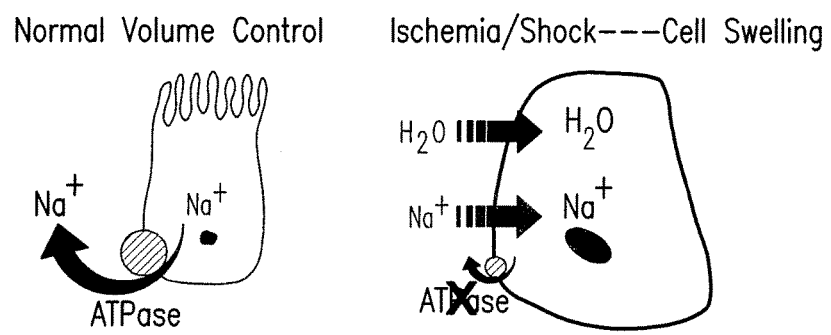
FIG. 1A-D. Proposed mechanism of action of cell impermeants in the non-energetic rebalancing of water movements during low volume shock states. A. The original defect is caused by the energy dependent collapse of the Na/K ATPase activity during shock due to low oxygen delivery and loss of ATP. As the pump fails, $Na^+$ enters the cell followed by water. B. Swollen parenchymal cells compress local capillary networks in the tissue that increase the resistance to capillary blood flow and further impede microcirculatory oxygen delivery. This allows local lactates to rise. C. Loading the interstitial space with cell impermeants like gluconate or raffinose prevents ischemia-induced water movement (swelling) by osmotically holding water in the interstitial space. This prevents capillary compression and preserves local exchange capacity, even under low volume conditions. D. The inclusion of an oncotic molecule with an impermeant establishes an osmotic-oncotic gradient between the intracellular-interstitial-capillary compartments, which promotes further the energy independent flow of water from the cell (where it shouldn't be) into the capillary (where it should be). The movement of capillary water with oncotic agents then increases capillary pressures that promote capillary flow even under low volume states. The sum effect is to promote effective and efficient capillary transport and oxygen delivery in the low volume state.
Figure 1B:
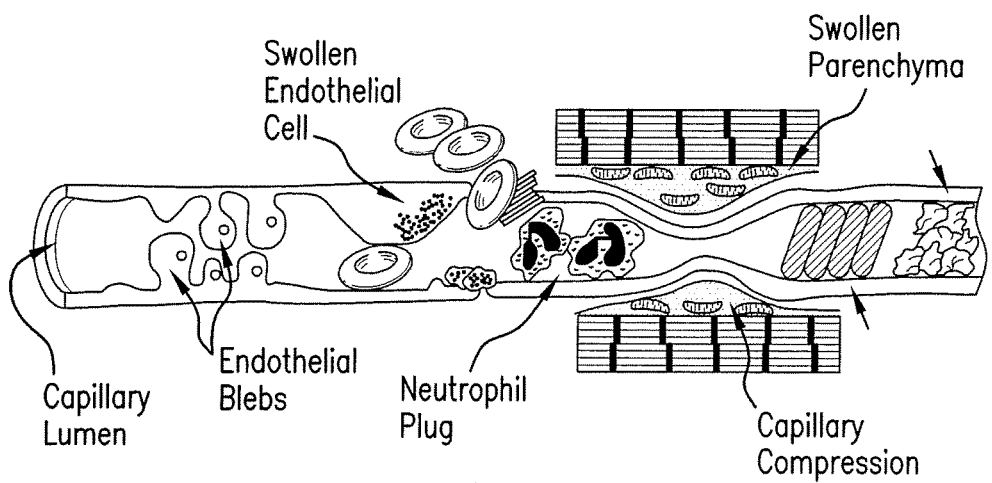
Figure 1C:
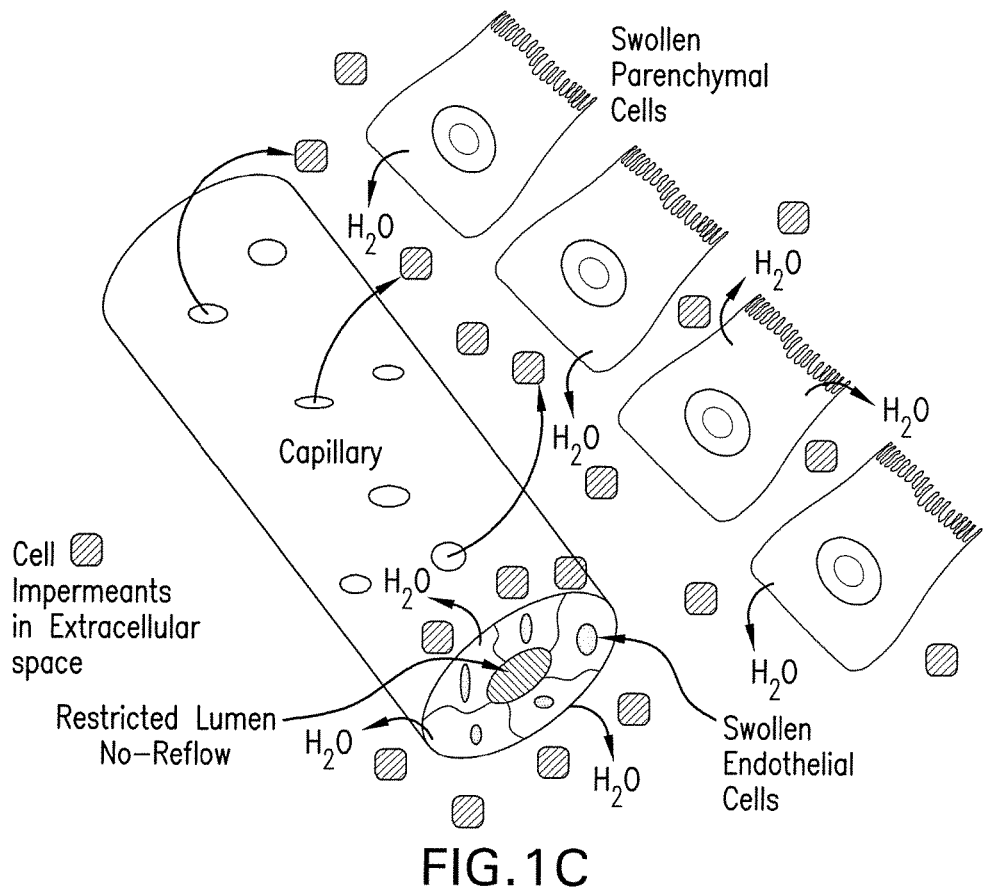
Figure 1D:
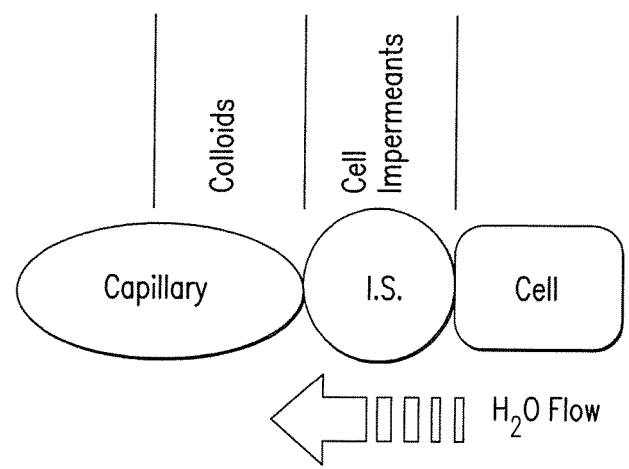

To reduce lethal cell swelling of tissues and organs during periods of shock or ischemia due to lack of oxygen delivery and oxygenation, an organ protectant solution containing highly concentrated polymers, saccharides and/or anions is provided to the patient as soon as possible. Cell swelling occurs during prolonged periods of shock when medical care is delayed. The organ protectant solution may also be given as a protectant for organs to patients in severe hemorrhagic shock and trauma so as to increase the "Golden Hour" before more definitive medical care can be given (e.g., soldiers on a battlefield before evacuation; patients being pulled from traffic accidents and transported to hospitals by paramedical personnel, etc.).

The organ protectant solutions of the present invention mitigate lethal cell swelling by two modes of action that may be used singly or in combination. The first mode is to preferentially load the extracellular fluid compartment with one or more "impermeant" molecules that are physically able to escape into the extravascular compartment, but which are impermeable to the cell membrane. This preferentially increases the osmotic force outside of the cell, thereby removing cell water accumulation or preventing water from moving into the cell. The second mode of action is to increase the oncotic pressure using one or more oncotic agent. An oncotic agent is a molecule that is restricted to the blood vessel or capillary and pulls water from the extravascular compartment into the vascular compartment. The benefits of the impermeant and oncotic molecules of the invention will become evident with further discussion of the characteristics and properties of each.

As used herein, the terms "impermeant molecules" or "impermeants" are used interchangeably, and refer to a variety of small molecules that are resistant to passing through cell membranes. The cell impermeant molecules are an active ingredient of the organ protectant solutions of this invention, and they may be present alone or in combination with oncotic agents, and/or other suitable constituents (e.g., preservatives, anesthetics, etc.). The molecular weight, size, and charge are specific attributes that allow the molecules to function as cell impermeants. That is, cell impermeants within the practice of the invention have a charge and/or molecular weight which permit them to freely pass across the capillary endothelium and into the interstitial space, but they are too large and/or charged to cross the cell plasma membrane. Thus, they preferentially load into the extracellular fluid compartment where they can exert osmotic effects on both endothelial cells and parenchymal cells.

Examples of cell impermeants used in the practice of the invention include specific anions and small saccharides such as sorbitol, gluconate, trehalose, lactobionate, maltitol, raffinose, and combinations thereof. These agents are dissolved in water or a buffer solution (vehicle) such as phosphate buffered saline (PBS), saline, etc., and administered by intravenous infusion (I.V.). They are given in amounts to increase the theoretical extracellular fluid compartment osmolarity of impermeants by 40-100 mOsm/kg. This may require solutions with impermeants of 10-60% by weight and require 250-1000 ml of solution (for a 70 kg adult patient). Of the various small saccharides tested, the combination of trehalose-raffinose gave the best results in preventing lethal cell swelling and maintenance of organ vital functions. Other anions and small saccharides may be used as impermeants in the practice of the invention, and organ protectant solutions can include a single impermeant or a mixture of impermeants together with other compounds suitable for the application (e.g., preservatives, anesthetics, etc.). The best impermeants are those with higher molecular weights (e.g., small saccharides or anion with a molecular weight of 342 g/mol or more is preferred). Further, the performance of the organ protectant solution is influenced by the concentration of the impermeants. In general, the organ protectant solutions should have impermeant(s) present at a concentration of 10-60% by weight, and 250-2000 ml (more preferably 250-1000 ml) of organ protectant solution would be required for a 70 kg adult patient (it being recognized that the volume may generally correspondingly be higher or lower depending on the patient size). As discussed in more detail below, the best results were obtained with organ protect solutions including the highest molecular weights at the highest concentration (100 mM or above).

The term "oncotic agent" as used herein refers to a molecule that exerts oncotic pressure, or colloid osmotic pressure, that pulls fluid into the circulatory system. It is the opposing force to capillary filtration pressure and interstitial colloidal osmotic pressure that balances out the tendency for fluid to leak out of the capillaries. In other words, the oncotic pressure tends to pull fluid into the capillaries. Loss of oncotic pressure and an increase in filtration across the capillary, results in excess fluid buildup in the tissues (edema). The large majority of oncotic pressure in capillaries is generated by the presence of high quantities of albumin which constitute approximately 80% of the total oncotic pressure exerted by blood plasma on interstitial fluid, but is lost with sudden reduction in blood volume. By definition, oncotic agents are confined to the capillary or intra-vascular space where they can restore sufficient oncotic pressure to maintain circulation of red blood cells that remain in the vessels of an individual suffering from blood loss, trauma or shock.

Examples of oncotic agents suitable for use include various polyethylene glycol (PEG) polymers. Experiments using PEG in organ preservation suggest PEG is nontoxic at high concentrations such as those used in practicing the invention. In some embodiments, PEG-20k is used as the oncotic agent because it provides a size and molecular radius sufficient to stay in the capillary space and act as an oncotic agent. However, it would be clear to one of skill in the art that PEG polymers that are smaller than PEG-20,000, as well as PEG with a larger size such as PEG-35,000 or higher may also be used, as long as the size is sufficiently large enough to stay in the capillary space and act as an oncotic agent. In some embodiments, the PEG molecule has a molecular weight of at least 4,000. There is evidence to suggest that PEG molecules also possess a salutary effect on cell membranes during ischemia. It has been observed that maintenance of intact cell membranes (or other indicators thereof) is enhanced in tissues and cells treated with the solutions that contain PEG molecules.

In some embodiments, molecules such as PEG exhibit properties of both a cell impermeant and an oncotic agent. As shown in the Examples herein, PEG-20k was found to behave as a hybrid where some escapes the capillary space to act as an impermeant to prevent water movement into the cell and a large portion of the molecule stays behind in the capillary to exert oncotic force that draws the interstitial water into the capillary. PEG-20k added to LVR solutions possesses both impermeant and colloidal properties that greatly improves outcomes in a low volume resuscitation model of severe hemorrhagic shock.

The term "volume expanders" as used herein refers to colloids, such as albumin, hydroethyl starch (HES), Hetastarch, and Hextend. The classical example of a volume expander is albumin. Albumin is the most abundant protein in the blood, and has been used in the prior art to expand the volume of circulating blood. Another example is HES, which has been used in clinical trials and as a commercial product (Hetastarch and Hextend) to expand blood volume. However, HES is a "dirty" product with many fragments. The fragmented portion of HES molecules is not necessarily restricted to intravascular spaces, making its effect unpredictable and limiting its usefulness as a clinical volume expander in patients.

The term "subject" or "patient" generally refers to any mammal, typically humans. The organ protectant solutions and methods described herein also have veterinary applications including, but not limited to, companion animals and farm animals.

There are some prior art organ preservation solutions that use molecules such as lactobionic acid or raffinose. However, these solutions are designed to completely flush and replace the extracellular compartment and will not work as an IV solution (and have not been designed to work as an IV solution). The invention differs markedly from organ preservation solutions of the prior art, in that the invention contemplates a solution formulation and methodology which introduces impermeants into the extracellular space in order to boost the concentrations of the impermeants in the patient to levels that are active for the purposes contemplated herein. The impermeant-based organ protect solutions of the present invention are effectively 5× impermeant solutions that when diluted into the patient's extracellular fluid, will raise the impermeant concentration to an effective level to prevent cell swelling. Other organ preservation solutions, which are not used in the manner described herein, may be viewed as essentially a 1× impermeant solution, and they work only when they completely replace the patient's extracellular fluid. That is, if these solutions were used as a low volume solution as described herein (something which they were not designed to do and were not previously used in this manner) the final cell impermeant concentration of the patient will be about 20% of an effective concentration and, therefore, will not work. Thus, it should be clear that other preservation solutions that have some agents which may be viewed as a cell impermeant (e.g., lactobionic acid and raffinose) were not designed to dose the extracellular compartment of the patient as contemplated herein, but were designed to replace it with a synthetic solution (i.e., they are best viewed as organ flush out solutions).

One mechanism of action for the organ protectant solutions of the present invention is to transfer water from cells to the interstitial spaces by loading the interstitial spaces with impermeants. A second mechanism of action is the transfer of water from the interstitial spaces into the vasculature, by means of oncotic molecules or agents that are restricted to the vessels and capillaries. This two-step transfer helps to prevent lethal cell swelling. The intracellular concentration of ATP drops in cells when they are deprived of oxygen. Consequent to this is the reduction or arrest of all chemical processes that require intracellular energy (ATP). One of those processes is active cellular volume control. Volume control occurs when the cell actively pumps sodium (Na) out of the cell. This also removes water. When these sodium pumps fail, due to lack of ATP, free sodium enters the cell down an electrochemical gradient, which is followed by electrogenic chloride, and then by osmotic water movement. This causes lethal cell swelling that causes direct cellular injury by cell membrane and mitochondrial injury, and causes further reductions in capillary blood flow and oxygenation (termed the NO REFLOW PHENOMENON) by swelling-induced compression of the microcirculatory exchange vessels (capillaries).

FIG. 1 schematically illustrates the mechanism of action of the organ protectant solutions provided by impermeants. FIG. 1A shows normal volume control in a cell is achieved by pumping sodium out of the cell, while, in contrast, when the sodium pump stops working due to lack of ATP, the sodium is not pumped out of the cell and the cell enlarges by osmotic water movement into the cell. FIG. 1C shows that the organ protectant solutions load the extracellular fluid compartment with molecules that are impermeable to the cell membrane. This increases the osmotic forces outside the cell, which in turn either or both removes water from the cells or prevents water from moving into the cell. As shown in FIG. 1, the impermeant molecules have a charge and/or molecular weight that permit them to freely pass across the capillary endothelium and into the interstitial space, but they are too large and/or charged to cross the cell plasma membrane. Addition of oncotic agents that are restricted to the capillary (or other vasculature) promotes transfer of water from the interstitial space into the capillary. It is then incorporated into the circulation, with the added benefit of contributing to the fluid volume therein.

A preferred embodiment of the invention is an organ protectant solution that is suitable for administration to an individual suffering from blood loss, trauma or shock. The clinical introduction of the solutions to reduce or prevent lethal cell swelling is via intravenous administration of organ protectant solutions. Organ protectant solutions can be administered to soldiers on a battle field or civilians in the field (e.g., at the scene of an automobile accident) during the low volume state while awaiting more comprehensive medical care. The organ protectant solutions, through preventing lethal cell swelling, buy precious time and allow for trauma care for the shocked patient.

The organ protectant solutions of this invention (i.e., cell impermeant and oncotic-based solutions) can be used whenever cell swelling due to ischemia may be a problem, for instance, during hemorrhagic shock and trauma before definitive resuscitation can occur. More broadly, the organ protectant solution may also be used in any hospital, birthing, surgical, ICU, or primary medical care center, where unexpected bleeding or hemorrhage or ischemic consequences of cardiovascular-cardiopulmonary failure might occur as a consequence of trauma, independent medical conditions, or a medical or surgical treatment.

Accordingly, organ protectant solutions have exemplary uses in:

1. Combat casualty care: The military use for organ protectant solutions may indeed be great. Most injuries and deaths on the battle field are due to severe hemorrhagic shock and trauma secondary to blast injury and high energy projectile impacts. Soldiers must be treated in harsh conditions with low volume resuscitation using simple solutions that are chemically stable in extreme temperature conditions. Cell impermeant-based low volume resuscitation solutions fit the bill. They have been shown to extend the time that a subject can remain in the low volume state, which extends the "Golden Hour" and would allow higher percentages of severely injured soldiers to survive until they reach more definitive trauma care at forward medical hospitals after evacuation from the field. Increasing the "Golden Hour" time 2-5 fold is possible and this would have a huge impact on mortality and morbidity.

2. Civilian trauma care: Severe hemorrhagic shock and trauma in civilian situations may typically arise from motor vehicle crashes, recreational accidents, and urban violence, among others. Severe hypotension and shock, even when successfully resuscitated, can often lead to secondary hemodynamic problems, infection, and multiple organ failure in the surgical intensive care unit. These patients often die from these secondary complications and there are no good effective treatments. Cell impermeant therapy, given at the time of initial resuscitation, may lower the incidents of these lethal secondary complications or reverse them if they are also administered at or around the time of their onset in the field. The organs that are particularly vulnerable in shock include the splanchnic organs (liver, intestines, and pancreas) and the lungs. Protecting these and other organs from lethal cell swelling may be key to mitigating secondary complications and multiple organ failure.

3. Sudden blood loss or hemorrhage occurring unexpectedly as a result of an otherwise routine medical or surgical procedure. Even when a surgical procedure is expected to be uneventful, complications or iatrogenic injury may occur and cause uncontrolled bleeding or loss of blood pressure. While some situations may include provision for rapid blood transfusion, many do not, particularly when conducted in ancillary or satellite facilities, such as a same-day or outpatient surgical center or birthing center. When a patient's condition becomes acutely grave, the typical course of action is to transport the patient to a hospital or trauma center where an escalated level of care can be provided. It is contemplated that administration of an organ protectant solution would provide a means of counteracting shock and reducing ischemia during the period of time when a patient is still in the ancillary medical center and during transport to a full-service medical center.

4. Surgical and medical ICUs where the consequences of a prior prolonged total body ischemia (shock) after full resuscitation cause global tissue energy crisis resulting in loss of energy-dependent volume control, cell and tissue swelling (especially in splanchnic organs), no reflow, and the development of critical illness. Critical illness is a condition characterized by abdominal compartment syndrome, systemic inflammation, loss of individual organ functions, multiple systems organ failure, sepsis, and death. It is contemplated that early administration of organ protectant solutions in the ICU to critically ill patients or those at high risk of developing critical illness in the ICU will prevent or rescue such patients by rebalancing internal organ volume control and re-establishing normal tissue perfusion.

5. Tissue preservation by administration to organ donors. Impermeant solutions, for example solutions including PEG polymers from 4,000-35,000 or larger, alone and/or in combination with gluconate, raffinose, trehalose, lactobionic acid, and sorbitol can be used to treat organ and tissue preservation injury by administration to organ donors (IV) after declaration of cardiac death (DCD-donation after cardiac death) and after declaration of brain death (DBD-donation after brain death). These solutions reduce preservation injury to transplanted organs including liver, kidney, small bowel, pancreas, pancreatic islets, lung, heart, heart-lung en-bloc, and skin when administered early (e.g. after declaration of cardiac or brain death) by one or more IV administrations to the donor over the cardiac or brain death period before organ retrieval. The solutions containing PEG polymers larger than 20,000 stabilize the hemodynamic state of the cardiac or brain dead donor by maintaining blood pressure and local circulation (by reducing cell swelling) thereby reducing the amount of needed support drugs given to these patients before organ retrieval to keep them alive.

6. In other aspects, the disclosure provides compositions and methods for use in preserving and/or reanimating organs ex vivo after removal from a donor, up until the time when the organ can be transplanted into an organ recipient.

By "preserving" we mean maintaining the state of an organ that is already functioning at a level that is suitable for use as a transplant, with no or minimal (e.g. about 10% or less, or about 5% or less) of a loss of any measurable parameter. For example, for a heart, the myocardial oxygen consumption ($MVO_2$) is maintained within a range suitable for transplant.

By "reanimation" we mean maintaining an organ that is not fully functional, or is not functioning at a level that is suitable for use as a transplant, for a period of time and under conditions that permit organ repair (rejuvenation, regeneration, etc.). For example, the organ may exhibit a loss of at least about 10% or more (e.g. about 20, 30, 40, or 50% or more) of any measurable parameter. During the period of reanimation, the organ regains or improves functionality to a level at which it is suitable for transplantation. For a reanimated heart, a meaningful endpoint suggesting fitness for transplantation is reestablishment of myocardial work with low enzyme and protein release. For example, one or more of the following enzymes or proteins may be measured: troponin (e.g. troponin I (TnI) and troponin T (TnT), where normal levels are from about 0.0-0.10 µg/mL); creatine phosphokinase (CPK), also called creatine kinase (CK) (where normal is less than about 100 ng·ml, e.g. less than 20-60 ng/ml); CK variant CK-MB (normally undetectable); myoglobin (normal is e.g. less than about 100 ng/ml, e.g.

1-50 ng/ml); and others such as lactate dehydrogenase (LDH) where normal ranges are e.g. from about 140-280 units/liter; aspartate transaminase (AST) (where normal ranges are from about 10 to about 40 IU/liter; ischemia modified albumin (IMA), normal is about 70 U/ml; pro-brain natriuretic peptide (normal=about 100 pg/ml); and glycogen phosphorylase isozyme BB (normal ranges from about 1 to about 10 ng/ml). Preferably, the levels in a reanimated heart will be at or near normal levels e.g. exceeding normal levels recognized by those of skill in the art by no more than about 30, 25, 20, 15, 20, or 5% or less. The values may be within the normal range. For reanimated livers, a meaningful endpoint suggesting fitness for transplantation is the production of gallbladder bile (e.g. about >20 μl/min/100 g tissue weight) at a testing period before transplantation and after reanimation. For reanimated kidneys, the production of urine (e.g. at about >0.1 ml/min/100 g tissue weight) during testing before transplantation (using a perfusate with isoncotic force) is an indicator of reanimation success. The organ damage that is repaired or reversed may have occurred prior to donation (e.g. due to ongoing disease or aging of the donor); or as a result of the proximate causes of the death of the donor (e.g. accident, heart attack, stroke, etc.); or as a result of removal of the organ from the donor, or transport, handling, etc. of the organ during and after removal from the donor.

During the periods of ex-vivo perfusion with the compositions described herein, residual toxins and/or medications present in the donor organ may be advantageously removed or flushed from the organ, and longer periods of perfusion permit more thorough removal. Removal of the donor organs from the pro-inflammatory donor milieu in non-DCD donors is also advantageous. In addition, during perfusion as described herein, medicinal agents which assist in preservation and/or healing of damage to an organ may be provided to the perfused organ, for example, drugs that activate pro-survival signaling (growth factors, for example), drugs that activate mitochondrial biogenesis (SIRT1 [NAD-dependent deacetylase sirtuin-1] activators or Thyroxine for example), drugs that prevent mitochondrial oxidative injury (MitoQ, sulfide, iodide, selenide or other elemental reducing agents for example), drugs that inhibit cardiomyocyte hypercontracture (2,3-Butanedione 2-monoxime), drugs that inhibit inflammation (steroids, plasma serpins, enzyme inhibitors, colchicine, P2X7 and P2X4 blockers, NFKB and p38 inhibitors, TLR and MyD88 inhibitors, inflammasome inhibitors, inflammatory caspase blockers, and stable resolvins, for example), drugs that control calcium homeostasis (magnesium, calcium channel blockers, inhibitors of Na/H exchange, for example), drugs that inhibit proteolysis (protease inhibitors, for example), and drugs that inhibit apoptosis (Apoptosis Signaling Kinase and caspase inhibitors for example), drugs that modulate the autophagic pathway (including but not limited to rapamycin, metformin, valproic acid, chloroquine), antioxidant drugs (as Vitamin C and N-acetylcysteine).

According to the practice of the present invention, using the methods and solutions described herein, a donated organ can be successfully maintained for either preservation until transplant or for reanimation and then transplant, for a period time of up to at least about 24, 22, 20, 18, 16, 14, 12, 10, 9 or 8 hours, or fractional portions thereof (e.g. ¼, ½, ¾ etc. hours). As demonstrated herein, in some aspects, the organ can be maintained in a transplant-acceptable state for at least about 8 hours, although periods of time of less than 8 hours are not excluded (e.g. 1, 2, 3, 4, 5, 6, or 7 hours, or fractional portions of these).

Preservation/Reanimation Solutions

The preservation/reanimation solutions provided herein generally comprise a molecule or molecules that possess hybrid characteristics whereby some of the active solute material is able to leave the capillary space to load into the interstitium to act as a cell impermeant while the remainder of the material stays in the capillary space to act as an oncotic agent. Exemplary molecules with these characteristics include those listed elsewhere herein. In particular, in some aspects, the molecule is polyethylene glycol 20,000 (PEG-20k), other similarly sized PEG polymers, or combinations of impermeants and colloids that serve the same biophysical roles as hybrid PEG polymers (albumin plus gluconate, for example).

If PEG-20k is utilized, it is generally present at a concentration of from about 1 to 5% (w/v), e.g. about 1, 1.5, 2.0, 2.5, 3.0, 3.5, 4.0 4.5, or 5% (w/v). In some aspects, the PEG-20k is present at a concentration of about 2.5% (w/v).

One or more sugars may also be included, for example, those listed elsewhere herein, and in particular glucose, mannitol, trehalose, rare sugars such as D-allose, sorbitol, gluconate, raffinose, maltitol, lactobionic acid, etc.

Buffering agents may be added to maintain the solution near or within a physiological range of from about 7.3 to about 7.5 (e.g. about 7.35 to about 7.45), e.g. one or more biologically compatible buffering agents such as HEPES, cholamine chloride, MPOS, BES, TES, DIPSO, phosphate salts of sodium or potassium, bicarbonate, Tris, etc.

In addition, one or more mineral sources are generally included. For example, potassium sources may be included, for example, $KH_2PO_4$, $K_2HPO_4$, KCl, K-Gluconate, etc. One or more cardioprotective agents that reduce the excitability of cardiomyocytes may also be included, for example, Mg salts ($MgCl_2$, $MgSO_4$, lidocaine, procaine, bretylium, etc.), as may agents that protect the myocardium from dangerously high levels of potassium such as $CaCl_2$, insulin, etc.

Agents that activate ATP synthesis may also be included, e.g. adenosine, adenine, ribose, phosphate, etc.

One or more antioxidants are typically included, for example, glutathione (usually reduced glutathione), elemental reducing agents like iodide or sulfide, Trolox (6-hydroxy-2,5,7,8-tetramethylchroman-2-carboxylic acid, a water-soluble analog of vitamin E), Vitamin C, Coenzyme Q10, e.g. in the form of MitoQ®, which is targeted to mitochondria, etc.

One or more agents that decrease xanthine oxidase activity may also be included, e.g. allopurinol, Febuxostat, etc.

In addition, hemoglobin or a synthetic hemoglobin substitute (e.g. Hemopure®) may optionally be included in the compositions, e.g. 2-6 g/dl and, in particular, should be added if the perfusion temperature is over 20° C.

Those of skill in the art will recognize that some agents may have a dual function in the solution. For example, Mg-gluconate acts as a Mg donor and the gluconate is an impermeant molecule; glutathione can act as an antioxidant when in reduced form, and as a source of glycine in either its reduced or oxidized form, etc. $KH_2PO_4$ provides both K+ and phosphate.

In exemplary aspects, a minimal preservation/reanimation solution includes: i) a hybrid molecule (e.g. 2% PEG-20k) that functions as both an oncotic agent and a cell impermeant, or a combination of molecules, at least one of which is an oncotic agent and at least one of which is a cell impermeant; ii) one or more sugars (e.g. gluconate, glucose); iii) one or more buffering agents (e.g. HEPES); iv) one or more mineral sources (e.g. a potassium source, a calcium source); v) one or more agents that decrease xanthine oxidase activity; and vi) one or more agents that activate ATP synthesis (e.g. adenosine, phosphate, and/or a short chain fatty acid such as octanoate), and an antioxidant (e.g. reduced glutathione), and in further aspects, the solution also includes hemoglobin or synthetic hemoglobin.

In some aspects, the solution includes: PEG-20K, $KH_2PO_4$, adenosine, Na-octanoate, Na-gluconate, $CaCl_2$ (dihydrate), and glutathione.

In some aspects, a known preservation solution is modified by the addition of a hybrid agents as described herein e.g. PEG-20k, to improve the preserving properties of the solution and/or by replacing any oncotic agents therein (e.g. HES) with those listed herein. Exemplary known solutions that can be so-modified include but are not limited to: Collins solutions, which contains high concentrations of potassium, magnesium, phosphate, sulphate, and glucose; Euro-Collins solutions, which contain high concentrations of potassium (110 mM), phosphate (60 mM), and glucose (180 mM); Ross-Marshall citrate solutions, the electrolytic compositions of which are similar to Euro-Collins solutions except that citrate replaces phosphate, and mannitol replaces glucose; Bretschneider histidine tryptophan ketoglutarate solution, which includes histidine (200 mM), mannitol (30 mM), tryptophan and alpha-ketoglutaric acid and low concentrations of sodium, potassium, and magnesium; Phosphate-buffered sucrose solution, which contains sucrose 140 mmol/L and sodium hydrogen and dihydrogen phosphate as buffers; University of Wisconsin solution, which has an osmolality of 320 mmol/kg and pH 7.4 at room temperature and is composed of: potassium 135 mmol/L, sodium 35 mmol/L, magnesium 5 mmol/L, lactobionate 100 mmol/L, phosphate 25 mmol/L, sulphate 5 mmol/L, raffinose 30 mmol/L, adenosine 5 mmol/L, allopurinol 1 mmol/L, glutathione 3 mmol/L, insulin 100 U/L, dexamethasone 8 mg/L, hydroxyethyl starch (HES) 50 g/L and bactrim 0.5 ml/L; Celsior solution, which contains sodium 100 mmol/L, potassium 15 mmol/L, magnesium 13 mmol/L, calcium 0.25 mmol/L, lactobionate 80 mmol/L, glutathione 3 mmol/L, glutamate 20 mmol/L, mannitol 60 mmol/L and histidine 30 mmol/L; and Kyoto ET solution which contains sodium 100 mmol/L, potassium 44 mmol/L, phosphate 25 mmol/L, trehalose 41 mmol/L, HES 30 gm/L and gluconate 100 mmol/L; and others. In general, such solutions are modified by the addition of hybrid agents such as PDG (e.g. PEG-20K and/or replacing any oncotic agents therein (e.g. HES) with those listed herein.

In an exemplary embodiment, the solution that is used is Belzer MPS®, which, without modification, contains adenine (free base) 5 mM, calcium chloride (dihydrate) 0.5 mM, dextrose (+) 10 mM, glutathione (reduced) 3 mM, HEPES (free acid) 10 mM, hydroxyethyl starch 50.0 g/l, magnesium gluconate (anhydrous) 5 mM, mannitol 30 mM, potassium phosphate (monobasic) 25 mM, ribose, D(−) 5 mM, sodium gluconate 80 mM, sodium hydroxide, 0.70 g/l, sterile water to a 1000 mL volume.

An exemplary modified solution comprises:

| | |
|---|---|
| PEG-20K | 2.5% (w/v) |
| $KH_2PO_4$ | 15 mM |
| Adenosine | 5 mM |
| Glucose | 10 mM |
| Na-Octanoate | 1 mM |
| HEPES | 12 mM |
| Mg-Gluconate | 5 mM |
| Na-Gluconate | 92 mM |

-continued

| | |
|---|---|
| $CaCl_2$ dihydrate | 0.5 mM |
| Allopurinol | 1 mM |
| Glutathione | 3 mM |

The glutathione that is present may be reduced or oxidized. In some aspects, since its action may be as a reducing agent and/or to contribute glycine, i.e. a glycine source is provided.

The exemplary modifications of Belzer MPS® include those which adapt the solution for use at higher temperatures than are typically used for organ storage, as described elsewhere herein. Such adaptations include but are not limited to: the use of adenosine instead of adenine; the addition of octanoate and allopurinol, changes in the concentration of some components, etc.

Those of skill in the art will recognize that the amount of each component of the exemplary composition that is present may vary somewhat, e.g. $KH_2PO_4$ ranges from about 5 to about 25 mM (e.g. 5, 10, 15, 20 or 25 mM); adenosine ranges from about 1 to about 10 mM (e.g. 1, 2, 3, 4, 5, 6, 7, 8, 9, or 10 mM); glucose ranges from about 5 to about 20 mM, e.g. about 5, 10, 15, or 20 mM); Na-octanoate ranges from about 0.1 to 2 mM (e.g. 0.1, 0.5, 1.0, 1.5 or 2.0 mM); HEPES ranges from about 5 to about 20 mM (e.g. about 5, 10, 15, or 20 mM); Mg-Gluconate ranges from about 1 to about 10 mM (e.g. 1, 2, 3, 4, 5, 6, 7, 8, 9, or 10 mM); Na-Gluconate ranges from about 75 to about 125 mM (e.g. about 75, 80, 85, 90, 95, 100, 105, 110, 115, 120 or 125 mM); $CaCl_2$ dihydrate ranges from about 0.1 to about 1.0 mM (e.g. about 0.1, 0.2, 0.3, 0.4, 0.5, 0.6, 0.7, 0.8, 0.9 or 1.0 mM); allopurinol ranges from about 0.1 to 2 mM (e.g. 0.1, 0.5, 1.0, 1.5 or 2.0 mM; and glutathione ranges from about 1 to about 5 mM (e.g. about 1, 2, 3, 4, or 5 mM).

Systems

Figure 13:
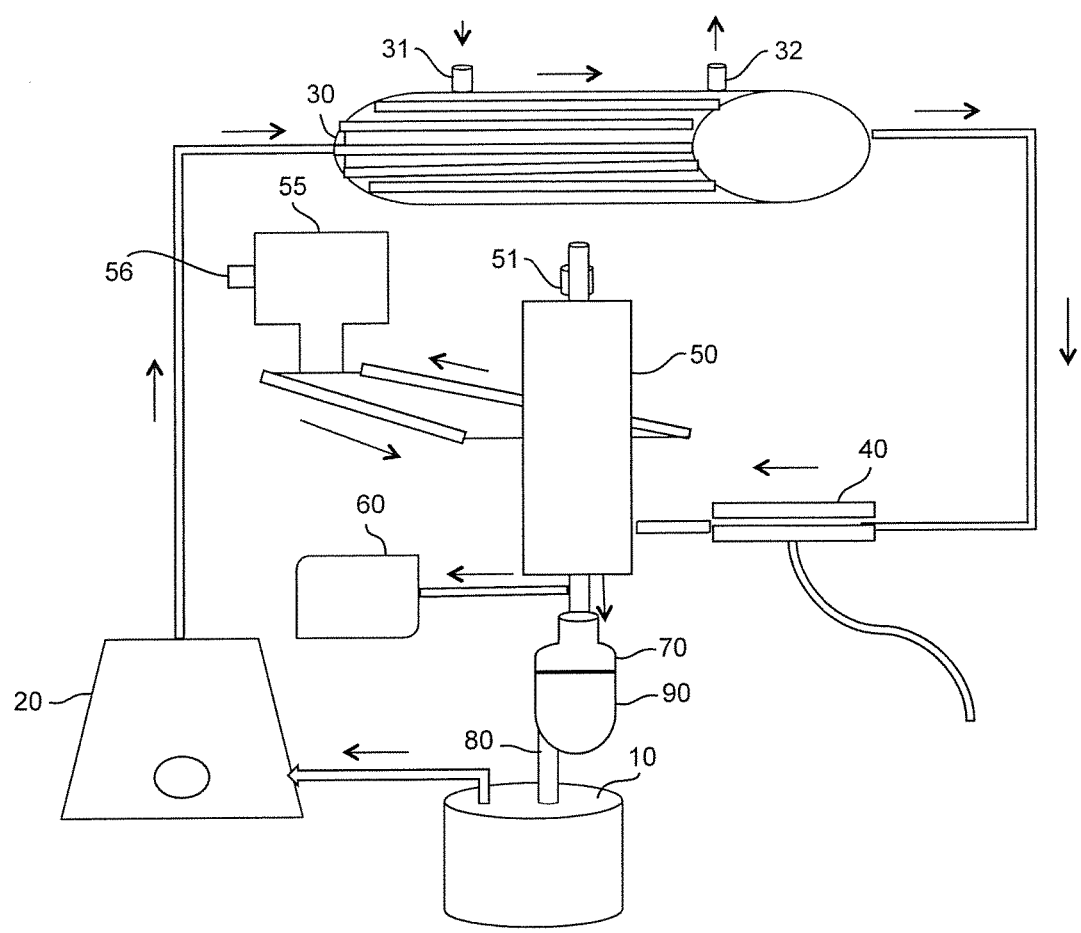
FIG. 13. Schematic representation of an exemplary machine perfusion system (MPS).

An exemplary machine perfusion system (MPS) which can be used in the practice of certain aspects of the invention is represented schematically in FIG. 13. The MPS has several components, usually added in series, to allow fine regulation of all the variables (e.g. temperature, flow rate, pressure, etc.). In the exemplary system depicted in FIG. 13, reservoir 10 contains the PEG-20K MPS solution and is connected to peristaltic pump 20, which allows flow regulation. The PEG-20K MPS solutions is pushed through oxygenation chamber 30 (with $O_2$ intake port 31 and gas exhaust port 32) to saturate the solution with 100% oxygen. The flow is measured by flow meter 40 and the temperature is regulated via heat exchanger 50 (with optional air trap 51), which is connected to water bath 55 (which has an associated temperature controller 56). Aortic (Ao) pressure is measured with pressure probe 60 connected to Ao cannula 70 through which the solution flows directly into heart 90. The solution circulates back through catheter 80 which is inserted into the inferior vena cava (IVC) of heart 90. Inflow and outflow solutions are collected at cannula 70 and catheter 80 to measure differences in $O_2$ concentration and to calculate the myocardial oxygen consumption ($MVO_2$). The arrows indicate the direction of flow.

Prior to use, the system is primed with a solution as described herein and air is removed from the system. The temperature is then regulated to perfuse an organ at a desired temperature, e.g. normothermic (e.g. about 37° C.), midthermic (e.g. from about 15° C. to about 21° C., e.g. about 15, 16, 17, 18, 19, 20 or 21° C.) or hypothermic (e.g. from about 2° C. to about 4° C.). In some aspects, the temperature range that is utilized is midthermic. A sample of the PEG- 20K MPS solution is analyzed to measure oxygen saturation, pH and ion concentration prior to use.

The following examples demonstrate the use of cell impermeants with or without oncotic agents in organ protectant solutions for hemorrhagic shock, trauma, and extension of the time during which an individual may be successfully resuscitated, treated and/or transported to a site where medical or surgical treatment can be provided, and more clearly show that the organ protectant solutions of the invention prevent or reduce lethal cell swelling. The Examples are provided to illustrate various embodiments of the invention, but should not be considered as limiting in any way.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

EXAMPLES

Example 1

Exemplary Formulation of Cell-Impermeant-Based Organ Protectant Solution

Table 1 presents the formulation of one example of a cell impermeant-based organ protectant solution according to the present invention. As discussed herein, the precise formulation of the cell impermeant-based organ protectant solution can vary within the practice of the invention. Specifically, the organ protectant solution should have one or more cell impermeants dissolved or dispersed in a pharmaceutically acceptable vehicle. The cell impermeant(s) will have a charge and/or molecular weight which permits them to freely pass across the capillary endothelium and into the interstitial space of a subject, but they are too large and/or charged to cross the cell plasma membrane such that they preferentially load into the extracellular fluid compartment where they can exert osmotic effects on both endothelial cells and parenchymal cells. They are given in amounts to increase the theoretical extracellular fluid compartment osmolarity of impermeants by 40-100 mM. This may require solutions with impermeants of 10-60% by weight and require 250-1000 ml of solution (for a 70 kg adult patient).

TABLE 1

| Cell Impermeants | Concentrations | g/L (1.5M) |
|---|---|---|
| Sorbitol | 0-1.5M | 273 |
| Gluconate (Na) | 0-1.5M | 294 |
| Trehalose | 0-1.5M | 513 |
| Raffinose | 0-1.5M | 891 |
| Lactobionate (Na) | 0-1.5M | 597 |
| Maltitol | 0-1.5M | 516 |
| Combinations | 0.4-1.5M Total | — |

Administration of approximately 0.5 liter is recommended per adult patient (assumed to be approximately 75 kg) to achieve the desired effect. The vehicle is phosphate buffered saline (PBS).

Example 2

Exemplary Method of Administration of the Cell Impermeant-Based Organ Protectant Solutions The general rule of thumb should be to start administration of the organ protection solutions as quickly as possible after the start of the ischemic event (e.g., hemorrhage due to trauma, cardiovascular collapse in shock). Give the solutions through an intravenous catheter like any I.V. fluid. For administration during shock, these solutions can be part of the resuscitation fluids. The solutions can be stored in convenient bags typically used for I.V. fluid, such as Viaflex, for storage, transportation, and use. Typical administered volumes may be in the range of, for example, 100-2000 ml, 100-1000 ml, 100-500 ml or 100-250 ml per patient, depending on the body mass and condition of the patient and the formulation of the solution. They also may be administered by constant infusion in the intensive care unit (ICU) during recovery from surgery and resuscitation. Alternatively, small amounts, such as 100-200 ml can be injected slowly into an IV line or vein using a needle of suitable gauge and a disposable syringe.

In any of the above described situations, it is also possible that there may be large numbers of victims, necessitating triaging decisions that require some patients to wait longer for transport to medical care. It is contemplated that prophylactic administration of organ protectant solution to patients who are identified for delayed treatment may be a prudent emergency treatment protocol if they are hypotensive and hypoperfused.

Example 3

Determination of Optimal Impermeant Molecules in an Organ Preservation Model A series of experiments were performed to explore the optimal impermeant effect of a family of likely useful impermeants. The variables are molecular species of impermeant, concentration (in the extracellular space), and time of administration. For these experiments, the impermeants used included specific anions and small saccharides such as sorbitol, gluconate, trehalose, lactobionate, maltitol, raffinose, and combinations of the same. These agents were dissolved in water of buffer solution such phosphate buffered saline and used in an in vitro tissue culture study.

Figure 2:
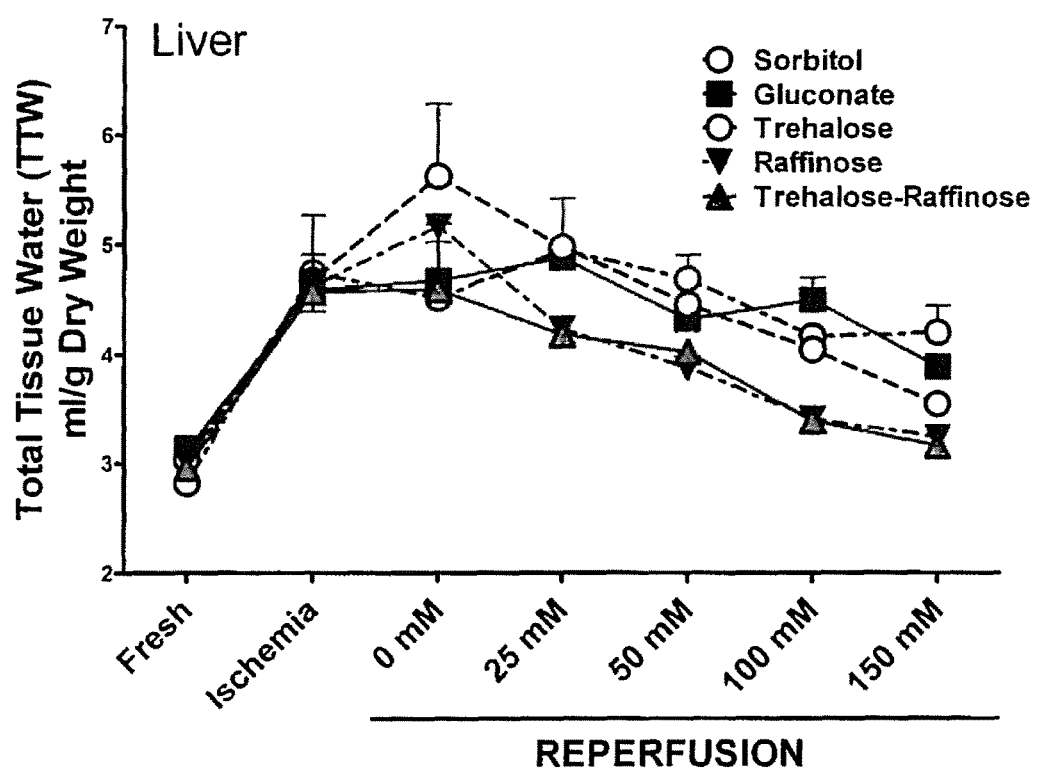
FIG. 2. Graph showing the effects impermeants have on swelling of liver slices.

FIG. 2 illustrates the effect of various impermeants on cell swelling of liver slices. The outcome variable was cell swelling of liver tissue slices exposed to periods of warm ischemia and reperfusion to mimic the conditions that a DCD donor liver would encounter in order to determine which solutions would minimize in vivo cell swelling. For these experiments, the best impermeant solution had the highest molecular weight and highest concentration (e.g., trehalose has a molecular weight of 342 g/mol, and best results were obtained with concentrations of 100 mM or above). However, combinations of high and moderate molecular weight impermeants also proved to work well.

In this model, liver tissue weight almost doubled after ischemia due to cell swelling from water accumulation. Cell impermeants in the extracellular space largely prevented or attenuated this increase. From these in vitro data, an optimized impermeant for in vivo treatments may include mixtures of trehalose and raffinose at about 50 mM each.

FIGS. 3A and 3B show the effect of cell-impermeant based organ protection solutions on a DCD model for liver donation to determine parameters for preventing liver failure in vivo in transplant patients. Adult donor rats were anesthetized and a bilateral pneumothorax was induced, which caused heart failure in 2 minutes. Then, 30 minutes of time was allowed to elapse to simulate warm ischemia in the DCD patients. At the time of heart failure, animals were assigned to either a control group that received about 3 ml of PBS vehicle I.V. over 10 minutes or an experimental group that was given about 3 ml of a trehalose and raffinose solution or a gluconate solution in PBS (about 750 mM each), I.V. over 10 minutes. Each animal also was given heparin and phentolamine at the time of cardiac death. After 30 min of in-situ warm ischemia, the liver was harvested and flushed with UW solution and cold stored for 24 hours. The livers were reperfused on an isolated perfused liver preparation (IPL) in-vitro for 60 minutes to assess post-reperfusion liver function (preservation injury). FIGS. 3A and 3B show vascular resistance and bile production for both groups, respectively.

FIGS. 3A and 3B show that treating DCD liver donors with impermeants in the peri-death period resulted in significant reductions in vascular resistance to flow and significantly increased bile synthesis at reperfusion (transplantation). Bile production in the early post-reperfusion period (the first hour after transplantation) is a highly predictive marker for later liver viability and life-saving function. These results clearly indicate less preservation injury with the use of cell impermeants in DCD donors. Since the end result of the experiment was a higher quality donor organ, the data are predictive for determining the likelihood of preventing organ failure when the solutions are used to treat individuals suffering from blood loss, trauma or shock.

Example 4

Hemorrhagic Shock Model in Rodents

Gluconate was administered in the organ protectant solution (e.g., a low volume resuscitation (LVR) solution with cell impermeants according to the present invention) in order to achieve a theoretical gluconate concentration of about 60 mM in the extracellular fluid compartment (subsequent experiments have shown that about 100 mM is probably optimal). The idea of low volume resuscitation is to give the shocked patient small volumes of intravenous fluids to prolong the time on the field to allow for rescue and transport to a forward hospital where more definitive resuscitation can occur (due to fewer resource limitations). The purpose of the addition of the cell impermeants to the LVR solution (usually saline) was to increase this "down time" further, effectively increasing the tolerance to the low flow state and making it more likely that the patient can survive the wait to the hospital. Essentially, the objective is to increase the "Golden Hour".

Figure 4:
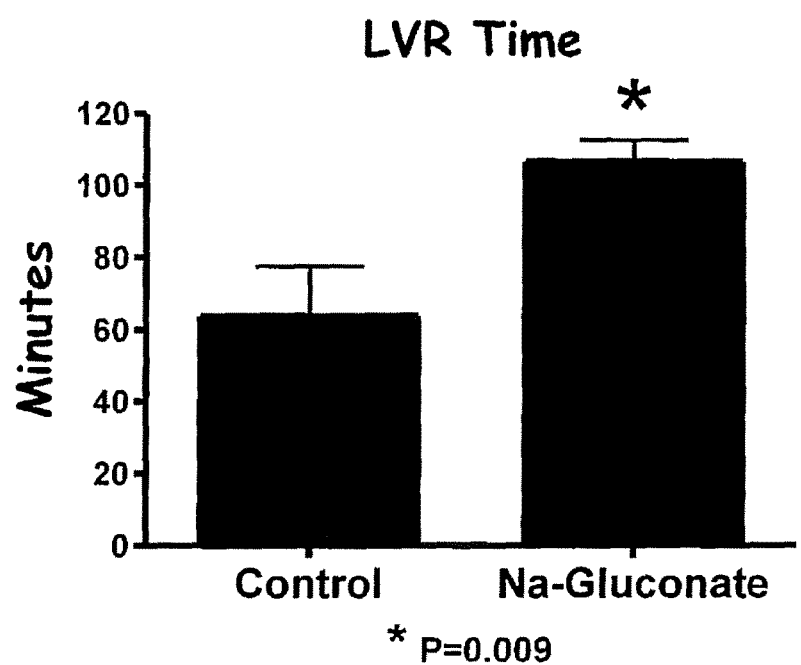
FIG. 4. Bar graph illustrating increases in the low volume resuscitation time with cell impermeants in an in vivo model.

FIG. 4 shows measurements of the LVR time period, a measure of the "Golden Hour". In shock experiments, the time that the control animals could remain in the low volume state (after LVR administration) was 64 minutes. However, gluconate added to the LVR solution significantly enhanced the LVR time to over 106 minutes. This means that these subjects were able to stay safely in the low volume state for much longer periods. In practical terms, they can wait longer for transport and full resuscitation, yet presumably have a higher chance of survival.

Figure 5:
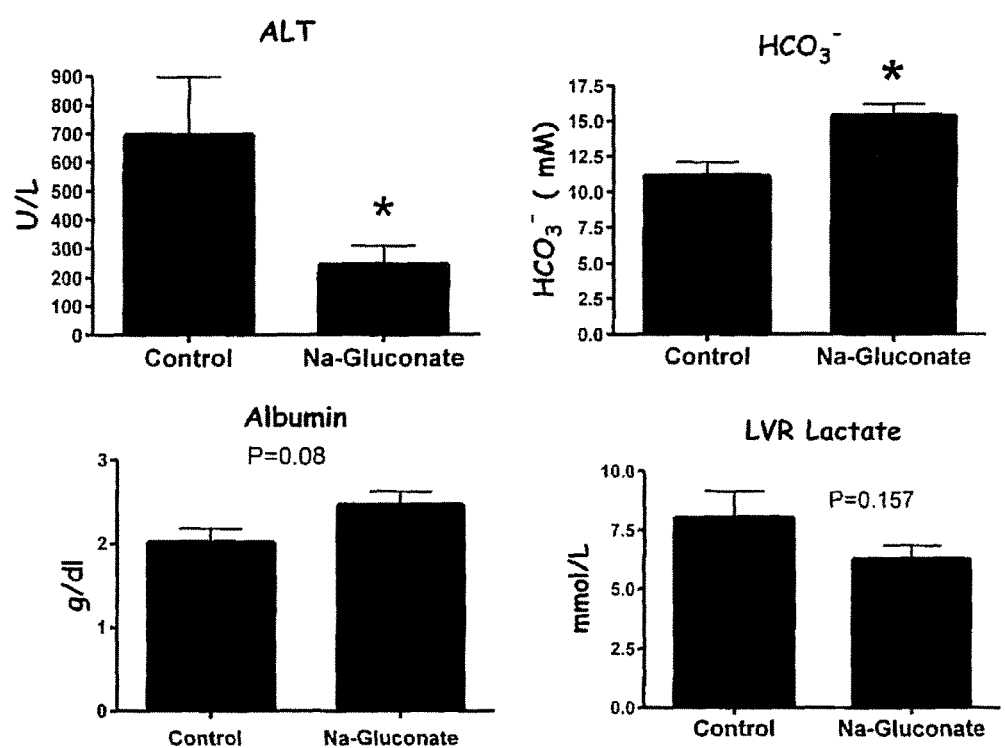
FIG. 5. A collection of bar graphs which show the effect of adding gluconate to low volume resuscitation (LVR) solution in liver enzymes, albumin, and metabolic acidosis.

In support of the determination that the LVR time is extended, gluconate-treated subjects also had less liver injury and better metabolism 24 hours after shock and resuscitation. This is shown in FIG. 5, which illustrates the beneficial effect of adding gluconate to LVR solution on liver enzymes, albumin, and metabolic acidosis. Liver enzymes were lower and albumin was higher in the gluconate group. Likewise, there was less metabolic acidosis in the gluconate group. Furthermore, the subjects in the gluconate group were kept in the low volume state much longer than the controls. Despite enduring much more hypotension (because the gluconate increased the low volume time), their condition as demonstrated by all parameters measured in FIG. 5 was improved the next day, compared to the controls.

Example 5

Use of Combinations of Impermeant Molecules and Oncotic Agent(s) in Organ Protectant Solutions In this example, an oncotic agent is added to the impermeants to observe and test the proposed convective amplification effect. Therefore, studies were conducted using the oncotic agent polyethylene glycol-20,000 (PEG-20k) with impermeant-based low volume resuscitation solutions disclosed above. Three groups of shocked rodents (described below) were included. LVR is initiated in all animals when plasma lactate reaches 10 mM, which is used as the definition of shock.

1. Saline controls: These animals received only saline as the low volume resuscitation fluid. The amount of LVR solution was 20% of the calculated blood volume, which is an equivalent of 1 liter in an adult human.
2. Impermeants-based LVR solution: These animals received combinations of the impenneants gluconate, raffinose, and trehalose at 10-25%, given at a volume of 20% of calculated blood volume.
3. PEG-20k-based impermeant LVR solution: This LVR solution contained both 10% PEG-20k and 15% gluconate (impermeant). For this group, the volume administered was cut in half to 10% of the calculated blood volume. This is equivalent to 0.5 liters for an adult human, and is within the dose range for a human with a body weight of 70-75 kg.

The main endpoint of this study was the low volume resuscitation (LVR) time, which is an indicator of the tolerance of the patient to withstand the low volume state during hemorrhage and trauma. The longer the LVR time, the longer an injured or traumatized individual can remain in the field before definitive medical treatment must occur. It is an approximation of the concept of the so-called "Golden Hour". As the golden hour increases, so does the ability to withstand periods of shock in the field before definitive resuscitation at a medical center or field hospital is required.

The converse is also true. Specifically, a longer golden hour greatly improves physiological function when a patient arrives at a hospital or trauma care center with conventional transport times. In these studies, the low volume resuscitation time is the time measured from the start of the LVR solution until the time when the plasma lactate level climbs back up to the critical value of 10 mM. At this time, full resuscitation must be given to avoid death. The invention provides an organ protectant solution that can expand the LVR time and provide more time for safe evacuation and definitive treatment at a qualified medical center or forward field hospital. It is also noteworthy that the combination of impermeant and oncotic molecules in the organ protectant solution provided better results with approximately half the volume of solution administered, compared to the volume of saline solution or impermeant solution.

Figure 6A:
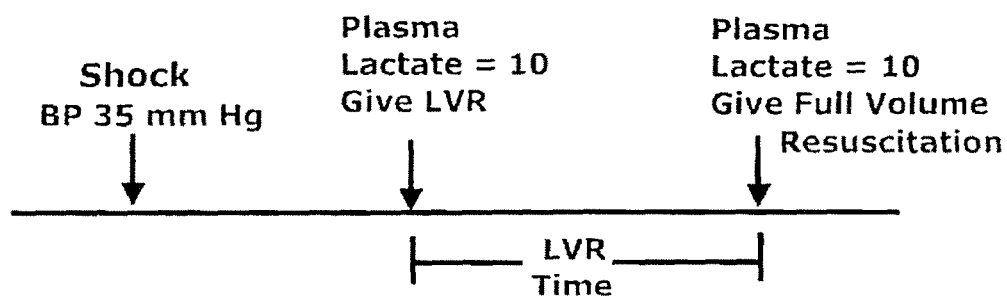
FIG. 6A-B. A) Timeline illustrating the concept of LVR time. B) Bar graph showing LVR times observed in 3 experimental groups of shocked animals.
Figure 6B:
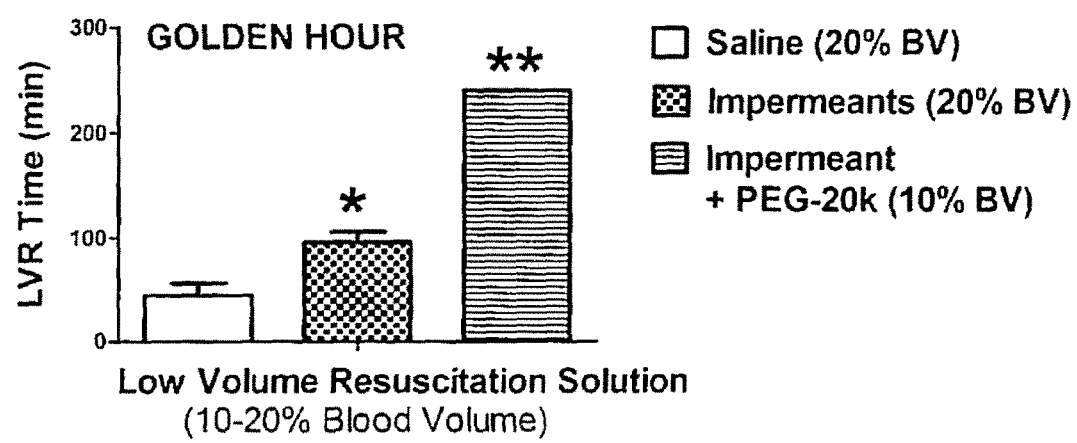

FIG. 6A shows a timeline illustrating the concept of LVR time progression, relative to blood pressure (BP) and plasma lactate as indicators of shock. FIG. 6B shows the actual LVR times observed in the three experimental groups of shocked animals. Animals receiving the PEG-20k-based impermeant LVR solution maintained a lactate level of 2.0 mM for 5-fold longer period of time beyond that animals receiving saline solution, and greater that 2-fold longer than animals receiving impermeants-based LVR.

Figure 7:
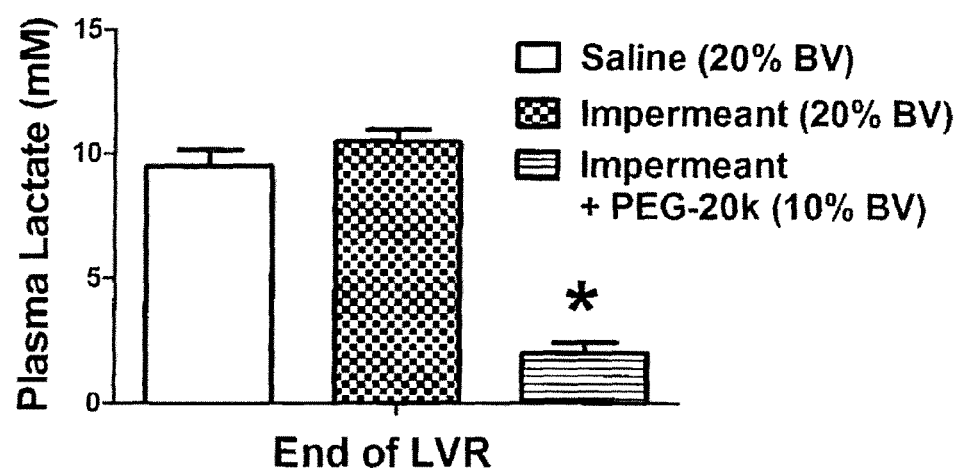
FIG. 7. Bar graph showing plasma lactate measured in 3 experimental groups of shocked animals at the end of the experimental LVR.

Example 4, showing the effects of a solution comprising impermeant molecules, is recapitulated in this study in the second group of subjects. The impermeant-based LVR solution doubled the LVR time seen with the saline controls in the first group of subjects. However, the impermeant effect was dramatically potentiated in the third group where PEG-20k (10%) was added to the impermeants. The LVR time was increased 5 fold above the saline control group. Furthermore, this was accomplished with only ½ of the volume (10% of the calculated blood volume compared to 20% in the other groups). Finally, the 4 hour LVR time was an artificial cut off since the real LVR time is much longer but still unidentified. The LVR times are defined by the time required for the patient to build more oxygen debt after administration of the LVR solution, as measured by the target lactate level of 10 mM. As shown in FIG. 6B, the PEG-20k-treated animals, which had a 5 fold higher LVR time, still had a plasma lactate of only 2 mM and were far away from the 10 mM target, shown in FIGS. 6B and 7. How much longer the animals could have remained in the low volume state until their lactate values reached 10 mM was not determined. However, this experiment demonstrates that administering a solution of both impermeant molecules and oncotic agents maintains protection from tissue and organ damage for at least 5 times as long as saline solutions and more than twice the time as can be achieved with impermeant-based solutions. In practical terms, this means that the time for resuscitation, treatment, and/or transport to a trauma center has been extended at least 5-fold, increasing from less than 45 minutes, to greater than 4 hours with administration of a solution of both impermeant molecules and oncotic agents.

Figure 8:
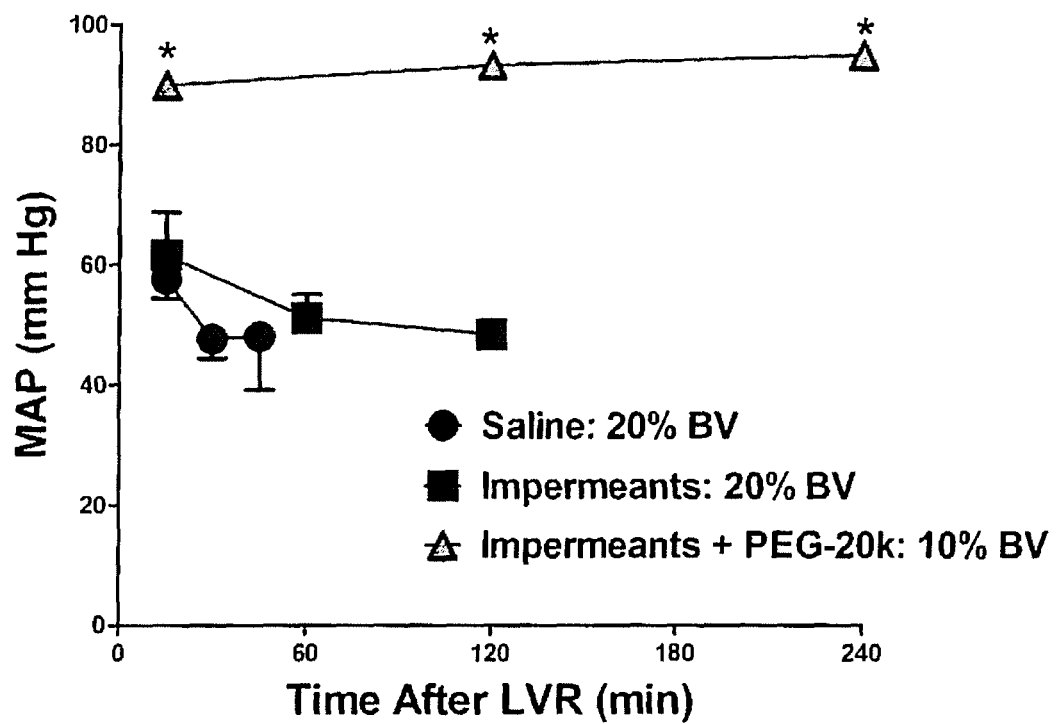
FIG. 8. Line graph showing mean arterial blood pressure (MAP) measured in 3 experimental groups of shocked animals.

Maintenance or restoration of blood pressure is a critical indicator of successful resuscitation and competent circulation, which is needed to oxygenate tissues and prevent ischemic injury. The mean arterial blood pressure (MAP) during the LVR period was much higher in the PEG-20k group, relative to the control and the impermeant group. FIG. 8 shows that while the other groups had a low and falling blood pressure during the LVR period, the PEG-20k group maintained blood pressure to normal values during LVR (with half the I.V. volume, relative to control saline or impermeant alone groups). In real life terms, this suggests a scenario where a severely shocked patient losing 50% of their blood volume that is given 500 ml of a PEG-20k-based impermeant LVR solution (I.V.) can remain in the field for 4-5 hours before being transported to the hospital where his cardiovascular and metabolic signs on arrival will still be essentially normal. The same patient given twice as much saline in the field (the current standard of care) will die from the same blood loss in only 45 minutes. Typically, the solution would be administered as an IV drip solution, with a volume of 500-2000 ml for an adult patient. These data also indicate that smaller volumes, such as 100 ml, 200 ml, 250 ml, 300 ml, or 400 ml would still extend LVR time and allow successful resuscitation and maintain circulation for a sufficient period of time to transport a patient to a site where definitive care can be provided.

Example 6

Use of PEG as an Oncotic Agent(s) in Organ Protectant Solutions

In this example, an oncotic agent is used alone to observe and test the effect of the colloid alone and to test different molecular species of PEG where lower molecular weight polymers may possess both impermeant and oncotic properties, and therefore, may be used without other impermeant agents. Therefore, these studies were conducted using the oncotic agent polyethylene glycol-20,000 (PEG-20k) and other polymers with lower molecular weight (PEG-10,000) or with higher molecular weight (PEG-35,000) as the low volume resuscitation solutions disclosed above. Groups of shocked (plasma lactate of 10 mM) rodents include:

1. Saline controls: These animals receive only saline as the low volume resuscitation fluid. The amount of LVR solution is 10% of the calculated blood volume, which is an equivalent of 0.5 liter in an adult human.
2. Impermeants-based LVR solution: These animals receive combinations of the impermeants gluconate, raffinose, and trehalose at 10-25%, given at a volume of 10% of calculated blood volume.
3. PEG-20k-based impermeant LVR solution: This LVR solution contains both 10% PEG-20k and 15% gluconate (impermeant). For this group, the volume administered is cut in half to 10% of the calculated blood volume. This is equivalent to 0.5 liters for an adult human, and is within the dose range for a human with a body weight of 70-75 kg.
4. PEG-20k-based LVR solution: This LVR solution contains 10% PEG-20k alone and demonstrates the effect of just the PEG without the other impermeants.
5. PEG-10k-based LVR solution: This LVR solution contains 10% PEG-10k alone and tests the effect of just the PEG without the other impermeants. A lower molecular weight of PEG demonstrates the effect of a hybrid impermeant and colloid effect alone.
6. PEG-35k-based LVR solution: This LVR solution contains 10% PEG-35k alone and tests the effect of just the PEG without the other impermeants. This size PEG provides only oncotic effects with no impermeant effects since the molecule stays within the capillary.

These studies can be used to identify the weight of PEG that may be used alone to achieve a hybrid impermeant and oncotic effect as well as describe the salutary effects of just the oncotic effect alone in PEG species that have pure oncotic effects.

Example 7

Use of the Impermeant Organ Protectant Solutions to Prevent the Early Signs of the Development of Ischemic Cholangiopathy in DCD (Donation after Cardiac Death) Livers Used for Transplantation In this example, an impermeant solution containing any one or a mixture of listed impermeant molecules (gluconate, raffinose, trehalose, sorbitol, lactobionic acid, maltitol) with or without an oncotic agent (PEG-20k or higher molecular weight) is infused into a DCD organ donor at the time of cardiac death or shortly thereafter (about 1-2 liters of solution). The solution may be circulated by continuing CPR. The liver and other organs are retrieved later, after experiencing 30-90 min of warm ischemia time, using conventional surgical techniques and cold organ flush solutions (UW solution). The livers and other organs are either cold stored or machine perfused using UW based solutions in the conventional way. The liver is transplanted and adequate function returns. The chance of ischemic cholangiopathy developing days or weeks later are lessened or prevented by the use of the impermeant organ protectant solutions. Studies done in adult rats show that the early liver lysis that occurs after transplantation (preservation injury) is lessened in the impermeant group, shown in FIG. 9A. FIG. 9B shows that DCD livers that were transplanted into recipient rats did not show signs of early ischemic cholangiopathy when treated with the protectant solutions since the total bilirubin levels did not significantly rise one week after transplantation, relative to the controls that were not treated at the time of liver retrieval. The data in this example indicate that the organ protectant solutions are able to salvage DCD livers and prevent or attenuate the development of what is most likely ischemic cholangiopathy, which currently limits the use of DCD livers in clinical transplantation today.

Example 8

New Low Volume Resuscitation Solutions Containing PEG-20k

Introduction

The predominant root mechanism of injury in hemorrhagic shock is energy failure. While global ischemia and reperfusion injury are causally based at many levels, they all arise from changes that occur when the cell energetics drops because of a loss of adequate microvascular oxygen transport and subsequent loss of aerobically produced high energy adenine nucleotides[9-11]. One mechanism of cell, tissue, and organ injury is cell swelling that occurs from the loss of ATP-dependent cell volume regulatory control mechanisms. In most cells, the single highest energy consuming process is the running of the Na/K ATPase pumps in the cell membrane. These pumps actively transport sodium ions out of the cell to maintain membrane potentials and to run numerous Na+-dependent facilitated membrane transport processes such as calcium, glucose, amino acids, and organic cation transporters. In the absence of ATP to run those pumps, as occurs in ischemia following hemorrhagic shock, the Na/K ATPase turns off and sodium enters the cell as it runs back down its electrochemical gradient. The elevated intracellular sodium futilely stimulates the sodium pump that can't run because of loss of ATP[12]. Chloride then enters the cell down an electrical gradient and water follows the sodium chloride down a developing osmotic gradient, which causes the cell to swell. Hydropic degeneration from energy failure damages membrane and mitochondrial structures[13], which may lead to cell death. Swelling of parenchymal cells can also compress local capillaries leading to further reduced capillary flow and oxygen delivery causing a self-amplifying cycle. FIG. 1 shows how this mechanism occurs and how novel cell impermeant molecules can passively reverse this dangerous water flow.

This basic mechanism of cell ischemic injury has been well described in organ preservation associated with transplantation[14-16]. Effective modern organ preservation solutions were developed around this concept and contain high concentrations of cell impermeants[17]. These are classes of non-toxic molecules, usually saccharides and small organic cations and anions, which are small enough to freely egress the capillary space in the microcirculation but are too large or too charged to cross the cell membrane. As such, they preferentially load into the interstitial space where they create an osmotic force that prevents the movement of water into the cell as the sodium concentrations rise during ischemia. They prevent lethal cell swelling. Cell impermeant, as a class of agents, are one of the most effective components of organ preservation solutions used today[18]. The University of Wisconsin solution contains high amounts of raffinose, lactobionic acid, sulfate, and phosphate, which all act as cell impermeants to prevent water movement. The Belzer-UW MPS solution uses gluconate and HTK solution uses both high concentrations of histidine and mannitol as impermeants. Water movement in organ preservation is slower than ischemia at normal mammalian temperatures because hypothermia is used to preserve organs, which slows down the process. Since cell swelling during ischemia induced by hemorrhagic hypotension also occurs[19] and at a much faster rate than in organ preservation because of the warmer temperatures, it was hypothesized that loading the interstitial space with nontoxic cell impermeants during the low volume period would prevent lethal cell swelling and increase the tolerance of the patient to the low volume state and improve outcomes at resuscitation. In fact, as described in Example 4, acute studies in rodents with severe hemorrhagic shock indicate that small cell impermeants double the tolerance of animals to the low volume state (FIG. 4)[20]. The study described in Example 5 further found that one particular molecule, polyethylene glycol-20k (PEG-20k) increased the tolerance to the low volume state 5 fold, compared to saline controls (FIG. 6B). It was hypothesized that PEG-20k superiority was due to the molecule behaving as hybrid where some escapes the capillary space to act as an impermeant to prevent water movement into the cell and a large portion of the molecule stays behind in the capillary to exert oncotic force that draws the interstitial water into the capillary. This was supported by observations that PEG-20k in LVR solutions also normalizes the arterial blood pressure in the low volume state immediately after administration (FIG. 8)[20]. These previous studies did not assess the effects of PEG-20k based LVR solutions in a survival model nor did it compare them to standard crystalloid solutions used today. This was the objective of the current study. It was hypothesized that PEG-20k added to LVR solutions possesses both impermeant and colloidal properties that greatly improves outcomes in a low volume resuscitation model of severe hemorrhagic shock.

Materials and Methods

Figure 10A:
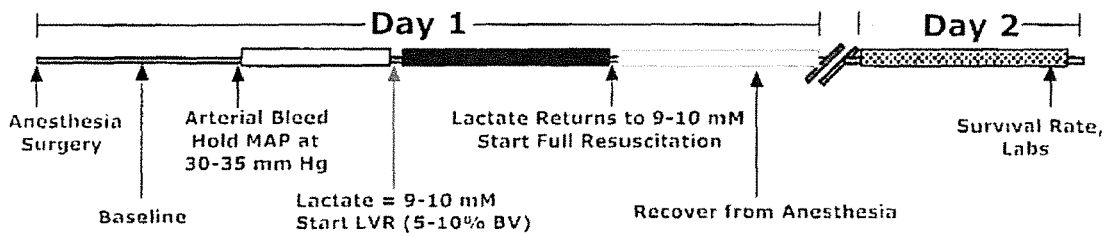
FIG. 10A-D. A) Diagram showing the shock, resuscitation, and recovery protocol used for these studies. The low volume resuscitation (LVR) time is the time from the start of the low volume resuscitation (after the lactate during hemorrhagic shock reaches 9-10 mM) until the time after the LVR infusion when the lactate rises back up to 9-10 mM again. This immediately precedes full resuscitation. The LVR time is a measure of the tolerance to the low volume state and is a function of the microcirculatory effectiveness since it is dependent on the rate of change of the plasma lactate. B) Low Volume Resuscitation (LVR) times for rodents in acute studies comparing the effectiveness of LVR solutions containing polyethylene glycol 20,000 (PEG-20k), Hextend, albumin, and saline controls. The numbers on the x-axis are the corresponding lactate concentrations in the plasma at the end of the LVR period. Most are close to 10 mM because that was the definition of the end of the LVR period. All agents were at a concentration of 5-20% by weight and were delivered at a volume equal to 10% or 5% of the calculated blood volume. * $P<0.05$ relative to all other values, all treated groups are significantly different from saline (control), all values are mean±SD, n=6-10 per group. C) Mean Arterial (blood) Pressure (MAP) measured at 15 min, 30 min, and at the end of the low volume resuscitation period for (6) groups of rats treated with various amounts of PEG-20k, Albumin, Hextend, or Saline as the low volume resuscitation solution. * $P<0.05$ relative to the other corresponding groups, # $P<0.05$ relative to all other corresponding values, n=6-10 per group, all values are mean±SD. D) The oncotic reflection coefficient ($\sigma_d$) for PEG-20k was measured in six rats to determine the impermeant and the oncotic effects of this molecule in both the mesenteric vascular bed and the thoracic bed. FITC-labeled PEG-20k was used as a tracer molecule and the reflection coefficient was determined by measuring the lymph (L) to plasma (P) concentrations of FITC-PEG after an IV injection of the tracer under conditions of high lymph flow induced by volume loading with I.V. saline infusions (0.25 ml/min). Lymph was sampled from a cannula placed into the thoracic duct to drain either the thoraces or the mesentery. FITC-labelled PEG-20k was measured by excitation-emission spectrofluorometry. The oncotic reflection coefficient was calculated as 1-L/P for PEG-20k at high lymph flow rates to make transport across the capillary totally dependent on convective solvent drag transfer and independent of diffusion. A coefficient of 1.0 indicates complete reflection back into the capillary and describes a pure oncotic agent. A reflection coefficient of 0 indicates no reflection at high lymph flow rates and describes a pure impermeant molecule (providing it is impermeant to cell membranes). The actual measured $\sigma_d$ for PEG-20k was about 0.60 in the thoracic tissues and 0.40 in the mesenteric tissues, which suggest the molecule is in fact behaving as a hybrid where some escapes into the interstitial space to act as an impermeant and a large amount of the material stays in the capillary where it behaves as an oncotic agent. The lower values in the mesentery is consistent with the known fenestrated "leaky" capillaries in the gut. The hybrid behavior is consistent with its physiological effects on blood pressure and low volume tolerance following shock. This property also explains why PEG-20k is effective by itself without classic impermeants (like gluconate) added with it. The values of $\sigma_d$ at each time point represent the average of 3 independent values from 3 animals for each vascular bed.

Rodent Shock Model: A low volume resuscitation (LVR) model was used in adult rats to test the impermeant based LVR solution used for pre-hospital resuscitation of rats with severe hemorrhagic shock. Adult Sprague Dawley rats were anesthetized with isoflurane and maintained in a light surgical plane of anesthesia during the study. Polyethylene catheters were placed in both femoral arteries for blood pressure monitoring and blood sampling and a catheter was placed in one femoral vein for administration of fluids. The animals were allowed to ventilate on their own to establish normal arterial blood gas (ABG) values. A 1-cm midline incision was created to induce soft tissue injury and for the placement of a temperature probe in the abdomen. The animals were kept at 38° C. using a heating pad and an incandescent light source above them. Arterial blood pressure, heart rate, and temperature were continuously recorded using a PowerLab® (ADInstruments, Boston, Mass.), a high performance data acquistion hardware. After a 30 min stabilization period, heparin was given (500 U/kg) and arterial blood was slowly removed at 1 ml/min into a syringe to maintain blood pressure at 30-35 mm Hg. This hypotension was maintained until the plasma lactate reached a value between 9-10 mM, as measured every 15 minutes with a hand held lactate analyzer (Lactate Plus®, Nova Biomedical, Waltham, MA) and every hour with a blood gas analyzer (Radiometer 800®). In preliminary studies, 9-10 mM was the highest plasma lactate level achievable without mortality during the LVR period. Once the target lactate was reached, a low volume resuscitation equal to 5-10% of the calculated blood volume[21] of saline was administered I.V. over a 10 min period using a syringe infusion pump. When the blood lactate again reached 9-10 mM, full resuscitation was started, which consisted of a volume of saline equal to the volume of the blood loss (about 55-60% of total blood volume) plus 30% of the removed red blood cells (washed) infused I.V. over 10 minutes. After 1 hour of full resuscitation, the animals were euthanized by an anesthetic overdose and terminal blood was removed for analysis. The time from the start of the LVR period until the start of full resuscitation is called the LVR time and it represents the tolerance of the animal to the low volume state or the maximum amount of time that a shocked subject can safely remain in the low volume state until more definitive resuscitation is required. This was a major outcome used in the study. In some experiments, survival from severe shock was studied with impermeant based LVR and compared to saline controls. In these studies, the animals were held in the low volume state for 180 min receiving either 10% saline as a control or 10% saline containing 10% PEG-20k impermeant. After 180 min, the animals were given full resuscitation and were awaken from anesthesia after the catheters were removed. These surviving subjects were studied the following day (24 hours) to determine the rate of survival, blood pressure, lactates, base excess, $PaO_2$ (A-a gradient), and other blood lab values. The shock and LVR protocol is illustrated in FIG. 10A.

Oncotic reflection coefficient: The oncotic reflection coefficient ($\sigma_d$) of PEG-20k in rodent capillaries was determined to characterize the biophysical characteristics of this impermeant in capillary networks. The $\sigma_d$ describes the relative convective solvent drag transport of a molecule across capillary pores. This characteristic is diffusion independent and is measured by determining the ratio of a compounds lymph concentration to the plasma concentration at high lymph flow rates. In these studies, rats were anesthetized as before and a PE10 cannula was introduced into the thoracic duct as previously described[22] to direct the lymphatic flow into a collection tube. Heavy cream (5-ml) was injected into the stomach to help visualize the duct after the lipid was absorbed. A saline infusion (I.V.) was started at 0.25 ml/min to accelerate lymph flow. Then, a single bolus injection of 5 mg FITC-labeled PEG-20k (Nanocs, New York, N.Y.) in saline was given. Blood plasma and lymphatics were collected every 10 minutes for an hour. FITC-PEG was then quantitated by direct measurement of the FITC fluor using a fluorescence plate reader (Biotek FL-800) with an excitation wavelength at 485 nM and an emission wavelength at 520 nM. The $\sigma d$ was estimated as 1-L/P of FITC-PEG-20k as previously described[23]. The values for $\sigma d$ are from 0-1 where 0 means no reflection into the capillary or complete freedom of passage through the capillary pores (impermeant characteristics). A $\sigma d$ of 1.0 means total reflection back into the capillary or complete oncotic properties.

Statistical evaluations of mean values were performed using parametric ANOVA with multiple comparisons corrections using the Dunnett or Bonferroni test for more than 2 groups or an unpaired T-Test for comparison of data with only two values (control and test group). Fisher's exact test was used for survival testing and A P value of 0.05 was set as a cut-off for statistical significance.

Results

Figure 10B:
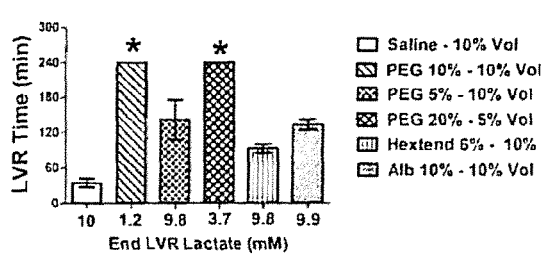

The effects of LVR solutions on the low volume resuscitation time are shown in FIG. 10B. The LVR time in this model is an index measuring the tolerance of the individual to the low volume state. It is the length of time that a patient can safely remain in the low volume state until definitive medical care and resuscitation is needed (golden hour), as indexed by the accumulation of a critical level of oxygen debt (lactate). Using normal saline (10% blood volume) as a control base crystalloid, the LVR time was determined to be about 30 min. Specifically, the time from the start of the low volume infusion (triggered when the patient accumulated a lactate of 10 mM) until the time when the patient re-accumulated the same lactate level, was determined to be an average of 30 minutes. This was significantly increased to 240 min (8 fold increase) when the same volume of saline contained 10% PEG-20k. Compared to PEG-20k, the LVR times for traditional resuscitation solutions such as 10% Hextend or 10% albumin were significantly lower. The plasma lactate at the end of the LVR period was close to 10 mM in all groups because this level of oxygen debt triggered the end of the LVR period by definition. However, the plasma lactate in the PEG-20k group at the end of 240 min was only 1.2 mM, which is far lower than the 10 mM trigger. Thus, the LVR time in the PEG-20k group (10%) was arbitrarily cut off and is a significant underestimation of its true value.

Figure 10C:
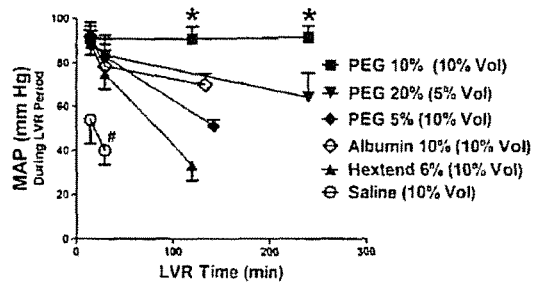

During the low volume state after the LVR solution is administered, mean arterial blood pressure was measured for the duration of the LVR period for a variety of LVR solutions (FIG. 10C). Saline solution (10%) resulted in low MAP values over the 30 min LVR time with values below 60 and 40 mmHg at 15 and 30 minutes, respectively. These pressures were improved with Hextend and albumin and completely normalized with PEG-20k (90-100 mm Hg).

Survival studies were conducted in a series of animals to determine the long term survival effects of impermeant based LVR solutions after a severe blood loss (55-60%) and a high accumulation of oxygen debt (lactate 10 mM). These results are shown in Table 2. All animals were required to undergo a controlled 180 minute LVR time with a 10% LVR solution following the hemorrhagic shock protocol (FIG. 10A). When saline was used, 0% survived for 24 hours and most died within 30-45 minutes after the LVR solution was administered. By comparison to the control, survival was 100% with the same volume of saline containing 10% PEG-20k.

TABLE 2

The effects of PEG-20k LVR solution on hemorrhagic shock values during the LVR period and after full resuscitation in survival animals.

| | During LVR | | | | |
|---|---|---|---|---|---|
| | LVR Time (min) | MAP (mm Hg) | Lactate (mM) | $HCO_3^-$ (mM) | $PaO_2$ (mm Hg) |
| Saline (10%) | 34 (18) | 49.3 (11) | 9.53 (2.1) | 11.9 (2.1) | 389 (72) |
| PEG-20k (10%) | 180 (0)* | 95.0 (3.5)* | 1.42 (0.6)* | 25.3 (3.4)* | 465 (31) |
| | Next Day Survival | | | | |
| | Survival (%) | MAP (mm Hg) | Lactate (mM) | $HCO_3^-$ (mM) | $PaO_2$ (mm Hg) |
| Saline (10%) | 0 (0) | NA | NA | NA | NA |
| PEG-20k (10%) | 100 (0)* | 85.6 (6.2)* | 1.2 (0.1)* | 25.6 (2.6)* | 475 (80)* |

Values are Mean (SD),
*$P < 0.05$, Relative to corresponding saline values, n = 5, $PaO_2$ measured with an $FiO_2$ of 0.9.

Furthermore, all of the animals that survived 24 hours after full resuscitation had normal blood pressure and arterial blood gas values, both during the 180 min low volume resuscitation period and after 24 hours of recovery. Saline treated animals had very low pressures during the LVR period, they demonstrated aberrant ABG values that were characteristic of severe metabolic acidosis, and they did not report 24 hour values since they all died during the LVR period.

Figure 10D:
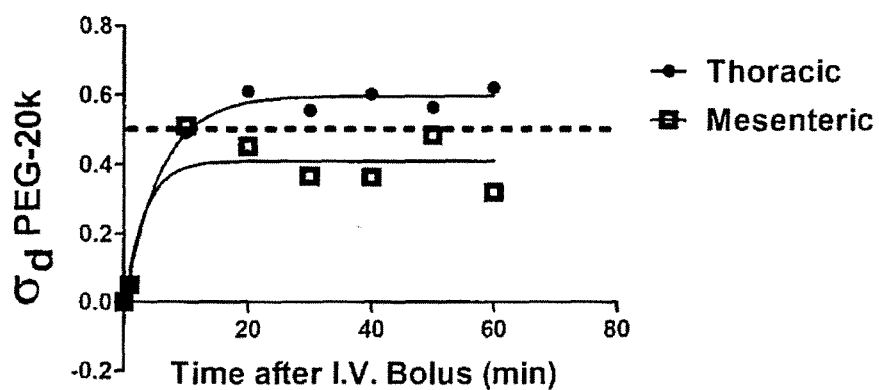

The capillary oncotic reflection coefficient for PEG-20k was measured in rats (FIG. 10D). The reflection coefficient was determined to be about 0.65, which indicates that some of the fluorescently labeled PEG-20k marker was pushed across the capillary into the interstitial space and lymphatics while much of the label was also clearly detected in the capillary space (plasma). The oncotic reflection coefficients were measured under high lymphatic flow rates by administering an intravenous infusion of saline during the 1 hour study. These conditions unmask the convective solvent drag transport potential of the tracer rather than the diffusional transport characteristics[24].

Discussion

Pre-hospital resuscitation of patients in the field with severe trauma and hypovolemic shock is challenging since the first responders are often forced to work with low volumes of simple crystalloid solutions that are both transportable and stable under field conditions. A recently described advancement in this area uses high concentrations of cell impermeant molecules in saline solutions as low volume resuscitation solutions for pre-hospital management of severely hypovolemic shock patients. In acute studies described herein, these solutions prevent ischemia-induced cell swelling, which alleviates both the harmful effects on cell and mitochondrial membranes and greatly improves microcirculatory capillary flow and exchange by preventing the occlusion of the microcirculation by swollen parenchymal and endothelial cells. This study extends those findings by testing the effects in survival shock models and compares these effects to crystalloid solutions that are considered standard of care in the field today. Finally, this study explores further the unique mechanism of action of PEG-20k, which has been determined to be the most superior impermeant molecule yet tested for low volume resuscitation in severe hypovolemic shock.

Cell impermeants are useful in severe shock because they load the interstitial space with osmotically active molecules that are impermeant to the cell membrane, but freely escape the capillary space. The increased osmotic force generated outside of the cell prevents intracellular water accumulation, cell swelling, and secondary capillary compression (FIG. 1). The addition of an oncotic agent to a cell impermeant solution was hypothesized to potentiate the effect of the impermeant alone by establishing a second oncotic gradient between the capillary space and the interstitial compartment, thereby augmenting the translocation of water accumulated in the interstitial space by the impermeants into the capillary space. This non-energetic movement of water into the capillary raises capillary pressure and increases capillary perfusion by both reducing the resistance to capillary flow (by preventing diameter changes from compression) and by increasing the capillary pressure gradient for flow. Surprisingly, the addition of the oncotically active impermeant, PEG-20k, to LVR solutions containing simple impermeants like gluconate geometrically potentiated the impermeant effect. The total response of the two components was reproduced by the PEG-20k component alone and much less than a pure oncotic agent alone (albumin). This suggested that PEG-20k may have a hybrid effect where the molecule acts both as a capillary permeable cell impermeant and as a traditional oncotic agent. Therefore, this study focused solely on the PEG-20k molecule.

An LVR solution containing 10% by weight of PEG-20k (given at 10% blood volume) has been shown to be optimal in our shock models. This was the gold standard to compare other solutions to size up their clinical potential. A 10% PEG solution given at 10% of the calculated blood volume (about 500-ml for an adult patient) produced the longest tolerance to the low volume state as compared to 6% Hextend and 10% albumin solutions. Since clinical formulations of albumin are generally about half strength (6% by weight), the values observed in this study probably are over-estimations of the effects observed clinically. Furthermore, the effect of the PEG-20k group has been significantly underestimated in this study since the LVR times were cut off at only 240 minutes, which is lower than the true LVR time because the trigger of 10 mM was never achieved in this group. Had the LVR time been increased until the lactate in the PEG-20k group reached 10 mM, the final LVR time would have been much greater than 240 minutes.

In a dose de-escalation trial, 10% PEG-20k given at either a lower volume (5% blood volume) of the same concentration (10%) or a lower volume (5%) at twice the concentration (20%) was compared. The lower total PEG-20k dose was less effective while the same dose but given at the lower volume was still very effective. This suggests that even lower volumes of LVR solutions can be achieved down to 5% of calculated blood volume. This is approximately 250-ml for an adult patient and may find use in combat casualty care on the battlefield where carry volumes of intravenous fluids for resuscitation are more of a concern.

The previous trials of impermeant based LVR solutions in shock were acute studies. The effects on survival are an important consideration for possible clinical use. When the LVR time was controlled to 180 minutes, all of the animals resuscitated with 10% PEG-20k as the LVR solution survived 24 hours compared to 0% survival in the saline control group. Furthermore, the surviving rodents were perfectly normal both in terms of physiological lab values and behaviorally. There were no apparent side effects of the PEG-20k LVR solutions except a temporary diuresis immediately after administration of the solution and a temporary metabolic alkalosis. Since PEG-20k acts as a hybrid molecule, it is likely that some of the material passes across Bowman's space in the glomerulus where it acts as an impermeant in the tubules to increase osmotic water clearance and cause a diuresis, similar to a mannitol effect. Furthermore, the increased excretion of water and likely electrolytes too, could prevent hydrogen ion reabsorption and increase renal acid excretion thereby causing a metabolic alkalosis. This is a favorable effect in shocked patients that are experiencing severe metabolic lactacidosis and obviates the requirement of bicarbonate administration to correct acidosis during resuscitation.

The impermeant effect in LVR solutions is greatly augmented when a colloid is also present. Since the putative colloidal agent, PEG-20k, works as well by itself as it does with typical small molecule impermeants like gluconate, it was hypothesized that this size PEG polymer may act as a hybrid and possess both impermeant and colloidal properties. To support this hypothesis, the capillary oncotic reflection coefficient for PEG-20k was measured in rats (FIG. 10D). The reflection coefficient was determined to be about 0.65, which clearly suggests that some of the material escapes into the interstitial space (impermeant characteristics) while a large portion of the material stays behind in the capillary to act oncotically. This strongly indicates a hybrid nature of PEG-20k, which supports the direct observations of its superior utility alone as an LVR solution and its apparent ability to cross the glomerulus to cause a diuresis. Further studies are needed to characterize the renal handling of PEG-20k but its combined impermeant and colloid effects are now well supported.

In conclusion, PEG-20k used at 10% weight and administered at 10% calculated blood volume during severe hypovolemic shock produces striking salutary benefits. These effects dramatically prolong survival in a controlled hemorrhage model and are due to the molecules hybrid impermeant and oncotic properties.

Example 9

Low Volume Resuscitation Solutions Containing PEG-20k in a Porcine Pre-Clinical Model Introduction The aim of the current study is to translate the effects of PEG-20k observed in the rodent model (Example 8) to a porcine pre-clinical model to demonstrate confidence in the use in patients. This report is a summary of 6 experiments in the swine model. Each group consists of 2 independent observations.

Materials and Methods

Juvenile swine (35-40 kn) were anesthetized with Ketamine/Xylazine, and propofol induction followed by isofluorane inhalation anesthesia maintenance (1-2%). A swan-Ganz catheter was introduced into the pulmonary artery via a cut down of the right jugular vein for the continuous measurement of cardiac output, pulmonary artery pressures, and sVO2 (mixed venous O2 saturation) by an optical sensor on the PA catheter. Blood pressure and arterial blood gases were measured by a line in the femoral artery. A line in the carotid artery and contralateral jugular vein was used for bleeding and resuscitation, respectively. The protocol was as follows:

Baseline measurements
Arterial bleed at 4 ml/kg/min by active pump withdrawal until MAP reached 35 mmHg
Subsequent bleeds at 2 ml/kg/min by pump withdrawal as MAP compensates (to about 45 mm Hg)
Total bleed to a lactate of 7-8 mM (about 2 hours and a blood volume loss of 62-65%)
Give low volume resuscitation by pump at 10% blood volume over 5 min of;
  a. Saline control
  b. 10% PEG-20k in saline
Monitor lactate until it climbs back to 7-8 mM. Mark the LVR time and record other parameters continuously or at 15 min intervals
Run PT-INR after LVR period
Run ex-vivo PT-INR of baseline blood samples after ex-vivo mixing with a 10% dilution of saline or a 10% PEG-20k solution.

Results

Figure 11A:
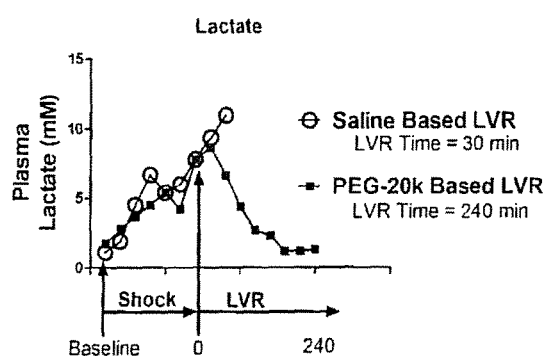
FIG. 11A-D. A) Line graph showing plasma lactate concentrations in pigs receiving a saline-based LVR solution or a PEG-20k based LVR solution. B) Bar graph showing LVR times in the two groups of pigs described in FIG. 11A. C) Line graph showing the mean arterial blood pressure of the two groups of pigs described in FIG. 11A. D) Line graph showing the cardiac output in the two groups of pigs described in FIG. 11A.
Figure 11C:
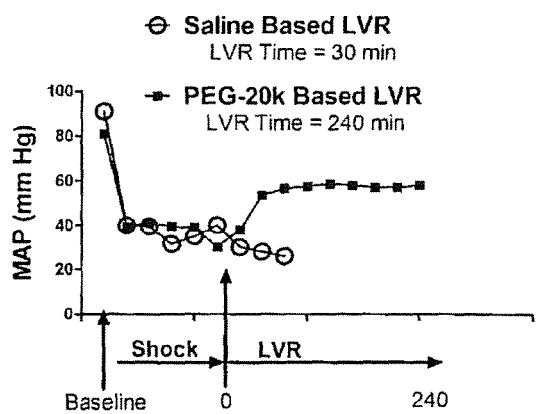
Figure 11B:
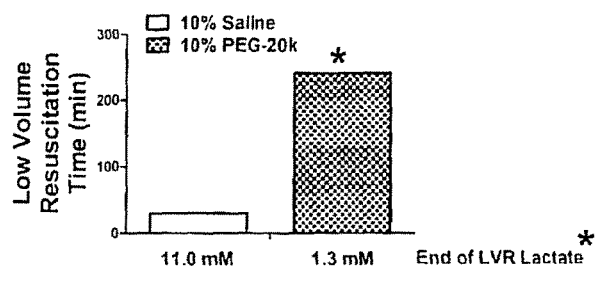

The plasma lactate concentrations (which are used as a surrogate for oxygen debt in these studies) in both groups of pigs is shown in FIG. 11A. In the group receiving saline as the LVR solution after shock, the plasma lactate never fell but continued to climb. This technically is an LVR time of 0 min. However, the group treated with PEG-20k (10% solution given at a volume equal to 10% of the calculated blood volume) showed lactates rising for the first 30 min period after LVR but then steadily declining over the next 3 hours to baseline values. Since the PEG-20k group showed an initial rise of lactate 30 min after LVR, the saline group was given the same consideration when calculating the LVR time (a pass on the first 30 min which represents wash out of uncirculated tissue lactate). This resulted in calculated low volume resuscitation times that were 8 fold larger in the PEG-20k group, relative to the saline control group. This is shown in FIG. 11B.

The mean arterial blood pressure was continuously monitored in pigs throughout the shock and LVR protocol. These data are shown in FIG. 11C. After saline LVR was administered, the blood pressure, already in the 30's due to the shock, never increased. When pigs were given a LVR solution containing 10% PEG-20k, the blood pressure rose to around 60 mm Hg and remained stable at that level over the four hour observation period after administration of LVR. Both groups of pigs were hemorrhaged the same amount of blood, between 62-65% of the total calculated blood volume.

Figure 11D:
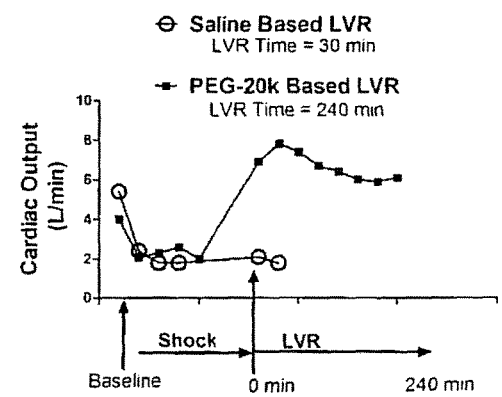

The cardiac output in the two groups of pigs was also monitored by thermodilution techniques using a Swan-Ganz catheter positioned in the pulmonary artery. The results are shown in in FIG. 11D. Cardiac output dropped to about 20% of the baseline value during shock and never recovered in animals given a low volume resuscitation with saline. However, PEG-20k LVR increased cardiac output above control values over the duration of the monitored LVR period. As the lactate fell and was cleared from the blood, the cardiac output slowly modulated downward toward the control values suggesting that the increased cardiac output was also increasing DVO2, which resolved the oxygen debt by restarting peripheral aerobic metabolism and reversing anaerobic glucose fermentation.

Figure 12A:
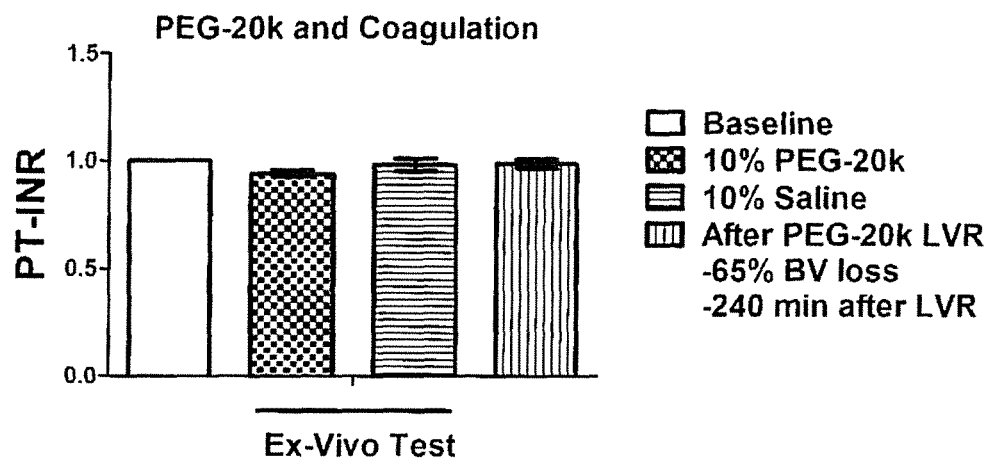
FIG. 12A-B. PEG-20k and coagulation. The (A) PT-INR and (B) aPTT effects were determined in both normal pig blood after ex-vivo mixing with PEG-20k LVR solutions (10% dilution) or with a saline control, also at a 10% solution, and after the end of the LVR period in pigs given PEG-20k based LVR solutions.
Figure 12B:
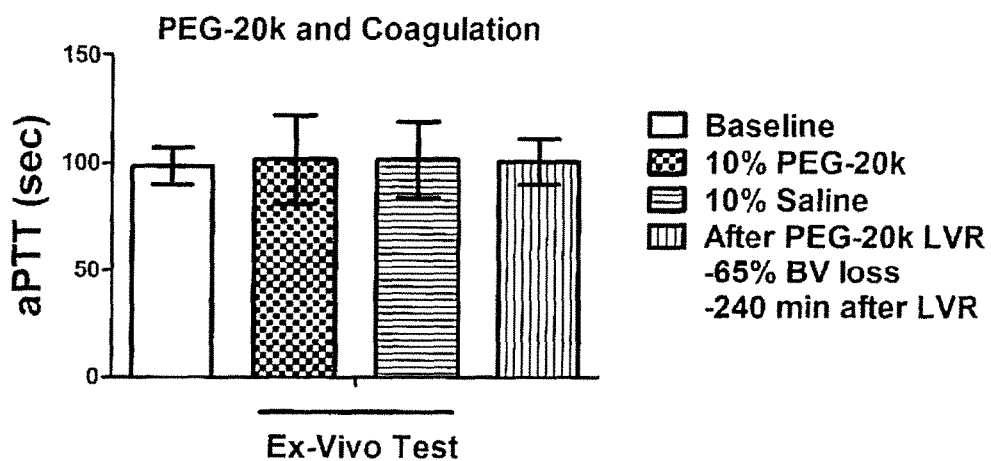

Finally, coagulation was determined in both normal pig blood after ex-vivo mixing with PEG-20k LVR solutions (10% dilution) or with a saline control, also at a 10% solution, and after the end of the LVR period in pigs given PEG-20k based LVR solutions. These effects are shown in FIG. 12A (PT-INR) and FIG. 12B (aPTT).

Coagulation was not altered either by the PEG-20k based LVR solution in an ex-vivo mixing test or in-vivo after giving a 10% blood volume infusion of PEG-20k as a low volume resuscitation solution. The most likely result of this finding is that PEG polymers do not interact with the enzymes and cofactors involved in the intrinsic and extrinsic coagulation pathways and the volume redistributing effects of the PEG based LVR solutions achieve oxygen delivery without the need for hemodilution (and secondary dilution of coagulation factors).

Conclusion

PEG-20k given at 10% concentration and a 10% calculated blood volume is effective at geometrically increasing (10 fold) the tolerance to the low volume state compared to saline controls in a large animal porcine model. This is characterized by rapid clearance of lactate, increase in mean arterial blood pressures to life sustaining levels, increase in cardiac output above baseline values, normalization of metabolic parameters, and maintenance of coagulation.

From the examples and description provided herein, it is clear that addition of an appropriate colloidal oncotic agent to the impermeant LVR solution dramatically amplifies the impermeant effect and increases the "Golden Hour" 5-fold at half of the administered volume. This is critical in battlefield or civilian pre-hospital settings where large volumes cannot be carried. Administration of an organ protectant solution containing impermeant and oncotic molecules also dramatically improves patient cardiovascular and metabolic function after prolonged periods of shock and low volume resuscitation.

Example 10

The treatment of choice for patients in end-stage heart failure is heart transplantation. Donor heart availability limits the use of this procedure and has given birth to new mechanical assist or replacement devices that are generally intended to bridge patients to heart transplantation by allowing them to survive on longer wait lists. While this approach works, the availability of more hearts would be welcome. These new hearts would likely enter the donor pool by expanding the current donor criteria and accepting hearts that are injured from warm ischemia (donation after cardiac death, DCD). However, these hearts are currently considered to be unusable and need to be reconditioned to improve function (reanimated) before they can be considered acceptable as transplantable donor organs.

Mechanisms of reanimation have focused on repair and replacement of severely damaged mitochondria in cardiomyocytes from DCD hearts because mitochondrial death is the most likely causative event in DCD heart dysfunction, based on preliminary data in human DCD heart recovery. A prolonged ex-vivo perfusion period between donor heart recovery and transplantation is required to affect mitochondrial repair or replacement through biogenesis. It may be possible to affect mitochondrial biogenesis (replacement) provided the reanimation period is long enough and provided the heart's metabolic needs can be maintained during that period. During this repair period, the myocardium must be adequately perfused. Currently, this is not possible because stable perfusion of the myocardium ex-vivo with existing perfusion preservation solutions (MPS) do not work. Typically, tissue edema and metabolic cell swelling occur early in heart perfusion, which limits adequate tissue oxygen delivery over the prolonged times that are needed for repair.

Therefore, the objective of these studies included development of a new perfusion platform for reanimating donor hearts ex-vivo that provided stable oxygen delivery over long periods of time under low pressure conditions with efficient capillary oxygen transfer to satisfy the metabolic demands of the tissue. To this end, both mid-thermic temperature machine perfusion and new cell impermeant strategies were employed. Mid-thermic temperature machine perfusion lowers the metabolic demands of the heart, and the new cell impermeant strategies non-energetically control cell and tissue water accumulation by secondarily decompressing the local capillary microcirculation to allow efficient capillary oxygen transfer.

A secondary effect of trying to achieve the main aim of heart reanimation was the development of a stable long term perfusion solution that preserves normal standard criteria hearts for twice as long as the current methods with superior performance. Currently, heart preservation uses cold storage at 2-4° C., which has an upper limit of only 4-5 hours. As surgeons approach this critical time period, the damage to the heart becomes directly proportional to the cold storage time; thus, it becomes increasingly difficult to insure that a heart will function properly after transplantation as the 4-5 hour cold storage time window elapses. If problems occur during surgery that lengthen the procedure, there is no functional reserve available and the heart will fail after transplantation. Therefore, a new preservation technique that doubles this preservation period in standard donor hearts without linear time dependent drops in function would be of great benefit for heart transplantation and would build provide a much needed safety window of time for the transplant procedure.

Purpose: The purpose of the study was to adapt the Organ Protectant Solutions used in-vivo to an ex-vivo perfusion platform to prolong the viable perfusion preservation of hearts for transplantation. Briefly, rodent hearts were recovered and perfused ex-vivo on a perfusion device for up to 8 hrs with Belzer MPS® ("MPS"=machine perfusion system) or a PEG-20k modified impermeant version of Belzer MPS® at mid-thermic temperatures (15 degrees and 21 degrees C.). Outcomes included perfusion and tissue oxygenation variables and myocardial tissue injury assessed by Troponin-1 enzyme release.

Methods and Results: The Belzer MPS® solution currently used to perfuse kidneys was modified in two areas; a non-specific modification consisting of addition of energy substrates glucose and octanoate to support metabolism at higher temperatures and a specific modification using a hybrid cell impermeant (PEG-20k) substituted for hydroxyethyl starch (HES) already present in the MPS solution. The PEG substitution is unique and critical to allow the heart to perfuse for at least 8 hours at 15-22° C.

Exemplary PEG-20K Modified Belzer MPS®

| Chemical | Concentration | MW (Da) | g/l |
|---|---|---|---|
| PEG-20K | 2.5% (w/v) | 20,000 | 25.00 |
| $KH_2PO_4$ | 15 mM | 136.09 | 2.05 |
| Adenosine | 5 mM | 267 | 1.34 |
| Glucose | 10 mM | 180.16 | 1.81 |
| Na-Octanoate | 1 mM | 166 | 0.166 |

-continued

| Chemical | Concentration | MW (Da) | g/l |
|---|---|---|---|
| HEPES | 12 mM | 238.3 | 2.86 |
| Mg-Gluconate | 5 mM | 207.3 | 1.03 |
| Na-Gluconate | 92 mM | 218.1 | 20.00 |
| $CaCl_2$ dihydrate | 500 mM | 147.1 | 0.074 |
| Allopurinol | 1 mM | 136.1 | 0.14 |
| Glutathione | 3 mM | 307.3 | 0.93 |
| Hemoglobin* (optional; cells or Hemopure ®) | 2-6 g/dl | | |

*No hemoglobin is required for perfusion temperatures up to 21° C., since the PEG-20k increases oxygen transfer so effectively. However, higher temperatures or safer perfusion at 21° C. (because at 21° C. we are right at the edge of Dcrit) necessarily requires an oxygen carrier.

| AMINO ACIDS<br>Amino acids from MEM amino acid mix from Sigma-Aldrich | Concentration (g/l) |
|---|---|
| L-Arginine (free base) | 10.0 |
| L-Asparagine•H2O | 2.84 |
| L-Aspartic Acid | 1.0 |
| L-Cystine | 2.5 |
| L-Glutamic Acid | 1.0 |
| L-Glutammine | 0.29 |
| Glycine | 0.5 |
| L-Histidine (free base) | 0.75 |
| Hydroxy-L-Proline | 1.0 |
| L-Isoleucine | 2.5 |
| L-Leucine | 2.5 |
| L-Lysine•HCl | 2.0 |
| L-Methionine | 0.75 |
| L-Phenylalanine | 0.75 |
| L-Proline | 1.0 |
| L-Serine | 1.5 |
| L-Threonine | 1.0 |
| L-Tryptophan | 0.25 |
| L-Tyrosine | 1.16 |
| L-Valine | 1.0 |

Adjust pH to 7.4 using NaOH 10N.
Adjust the volume to 1 L.

Perfusion Protocol:
Preparation of the Machine Perfusion System (MPS):

The MPS was primed with the PEG-20K MPS solution and air was removed from the system. The temperature was regulated to perfuse organs at a desired mid-thermic temperature (15° C. or 21° C.). A sample of the PEG-20K MPS solution was analyzed to measure oxygen saturation, pH and ions concentration.

Animal Preparation:

Eight to 10 week-old rats were anesthetized using Ketamine/Xylazine (100/10 mg/kg) and placed on the surgical table. Heparin (500 U) was injected through the tail vein and each rat was intubated after exposing the trachea and ventilated using a tidal volume of 8 ml/kg with a respiratory rate of 90 strokes/min. The chest was opened by cutting the ribs on each side of the chest and the sternum was flipped to allow complete exposure of the chest cavity. A 20G polyethylene catheter was then introduced in the inferior vena cava (IVC) and secured using a 4.0 silk ligated around the IVC. The heart was explanted and placed in cold 0.9% NaCl, and the aorta (Ao) was preserved, exposed by removing extra tissue and cannulated using a 18G cannula. The heart was weighed (subtracting the weight of the IVC and Ao cannulas) and connected to a primed machine perfusion system (MPS).

Heart Perfusion:

Antegrade heart perfusion with the MPS allows perfusion of the of the coronary circulation. A schematic representation of an exemplary MPS is illustrated in FIG. 1. For the present sent of experiments, the perfusion temperature was set to 15-22° C. Perfusion flow can be adjusted/regulated. Solution samples from the aortic (Ao) cannula and inferior vena cava (IVC) cannula were collected to determine the oxygen concentration and quantify the myocardial oxygen consumption ($MVO_2$) using the formula [($C_{Ao}O_2$−$C_{IVC}O_2$)/FI]×100, where $C_{Ao}O_2$) represents the $O_2$ concentration at the level of the Ao, $C_{IVC}O_2$ represents the $O_2$ concentration in the IVC and FI is the flow index, measured in [(ml*100 g)/min].

Figure 14:
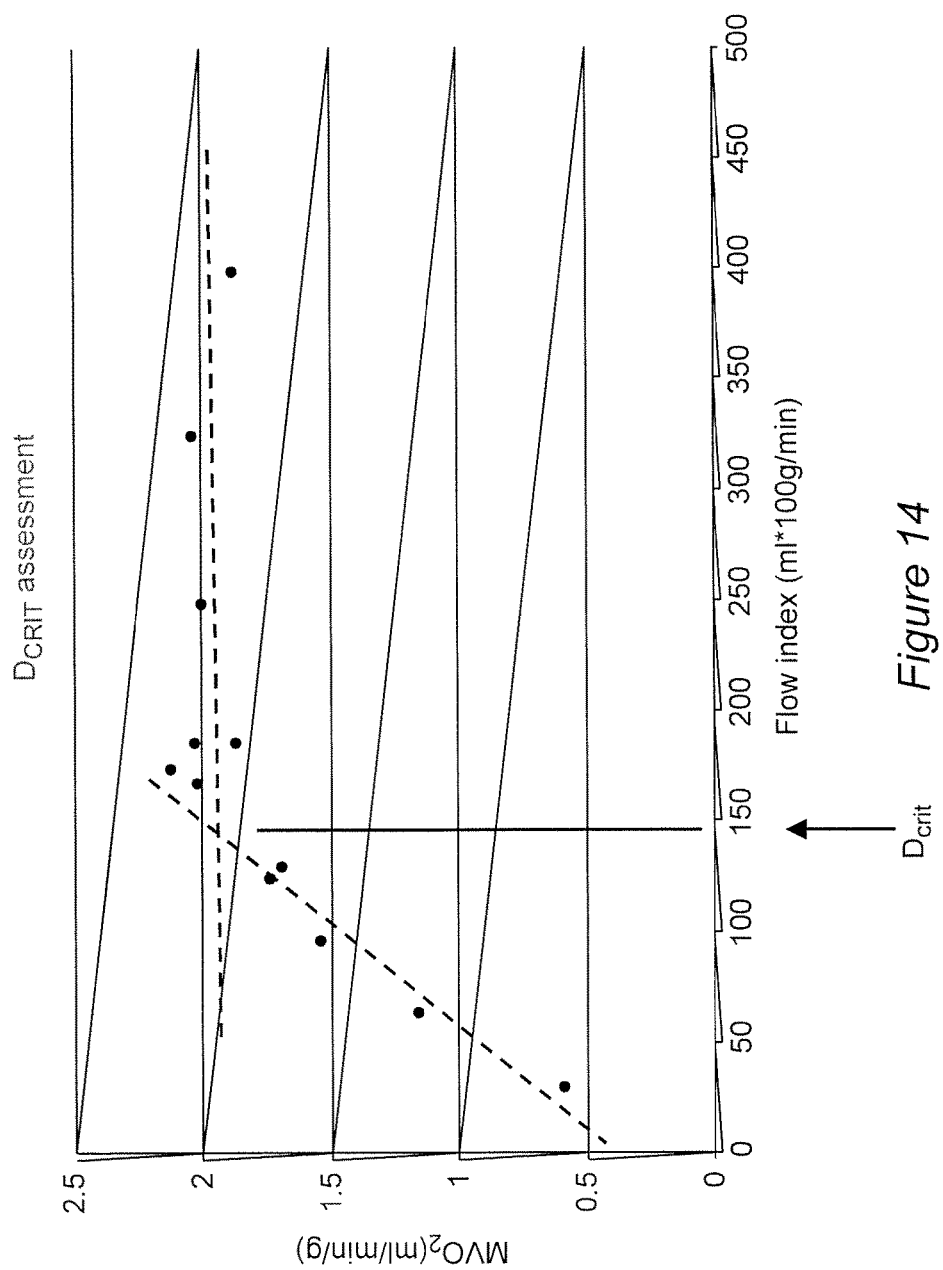
FIG. 14. Determination of the critical flow ($D_{crit}$) needed to maintain adequate myocardial perfusion and optimal myocardial oxygen consumption ($MVO_2$). The $D_{crit}$ was calculated by intersecting the lines corresponding to the plateau and the decline of the $MVO_2$.
Figure 15:
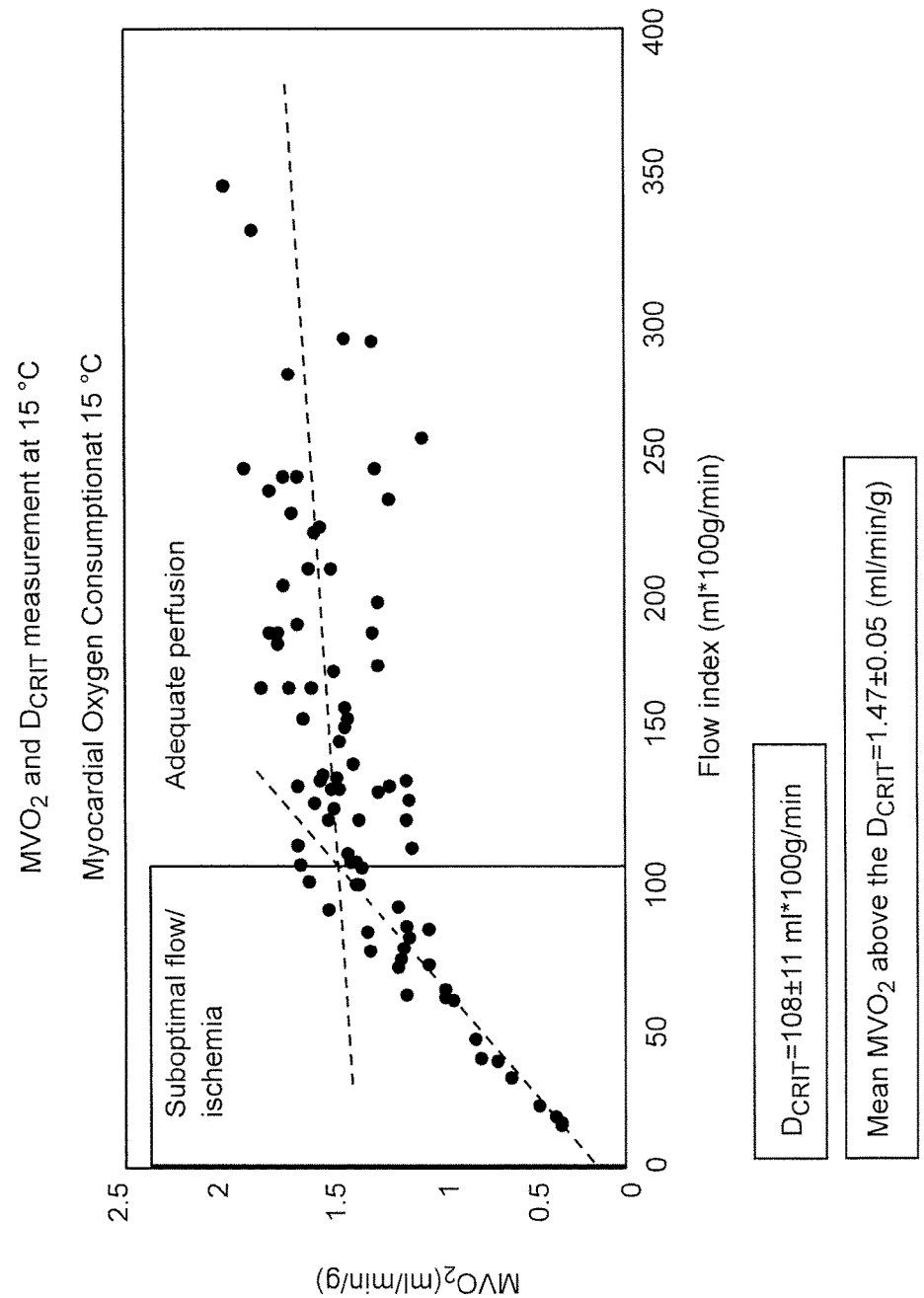
FIG. 15. $D_{crit}$ and basal $MVO_2$ were calculated for all the rat hearts perfused at 15° C. The boxed area delimits the field at which the flow index is insufficient to maintain the basal $MVO_2$.

Determination of the Critical Flow ($D_{CRIT}$):

In one set of experiments, organ perfusion was performed starting with high FI (400 ml*100 g/min) and the flow was decreased by 20-40 ml/min/100 g every 10 minutes. Solution sampling to measure the $MVO_2$ was performed at each FI. The values were plotted for each single heart and the $D_{CRIT}$ was calculated to establish the minimal required flow to meet the basal oxygen demand of the heart. A plateau phase, with stable MVO, is observed at the higher FI and a phase of decline of $MVO_2$ is observed when the FI falls below the $D_{CRIT}$ value. The $D_{CRIT}$ was calculated by intersecting the lines corresponding to the plateau and to the decline of the MVO, (as shown in FIG. 14); The data were collected together to determine the mean basal MVO, and mean $D_{CRIT}$ at 15° C. (FIG. 15).

Constant Perfusion for Organ Preservation:

The hearts were perfused at a FI above the $D_{CRIT}$ (i.e. 135 ml*100 g/min) for 8 hours at 15° C.; MVO, was measured every 2 hours, starting at time 0, to confirm adequate tissue perfusion. The initial (time 0) and the final (time 8 hours) $MVO_2$ are reported in FIG. 16 and suggest a metabolic steady state exists during the 8 hour preservation period because the initial and end MVO, values were the same.

Figure 17A:
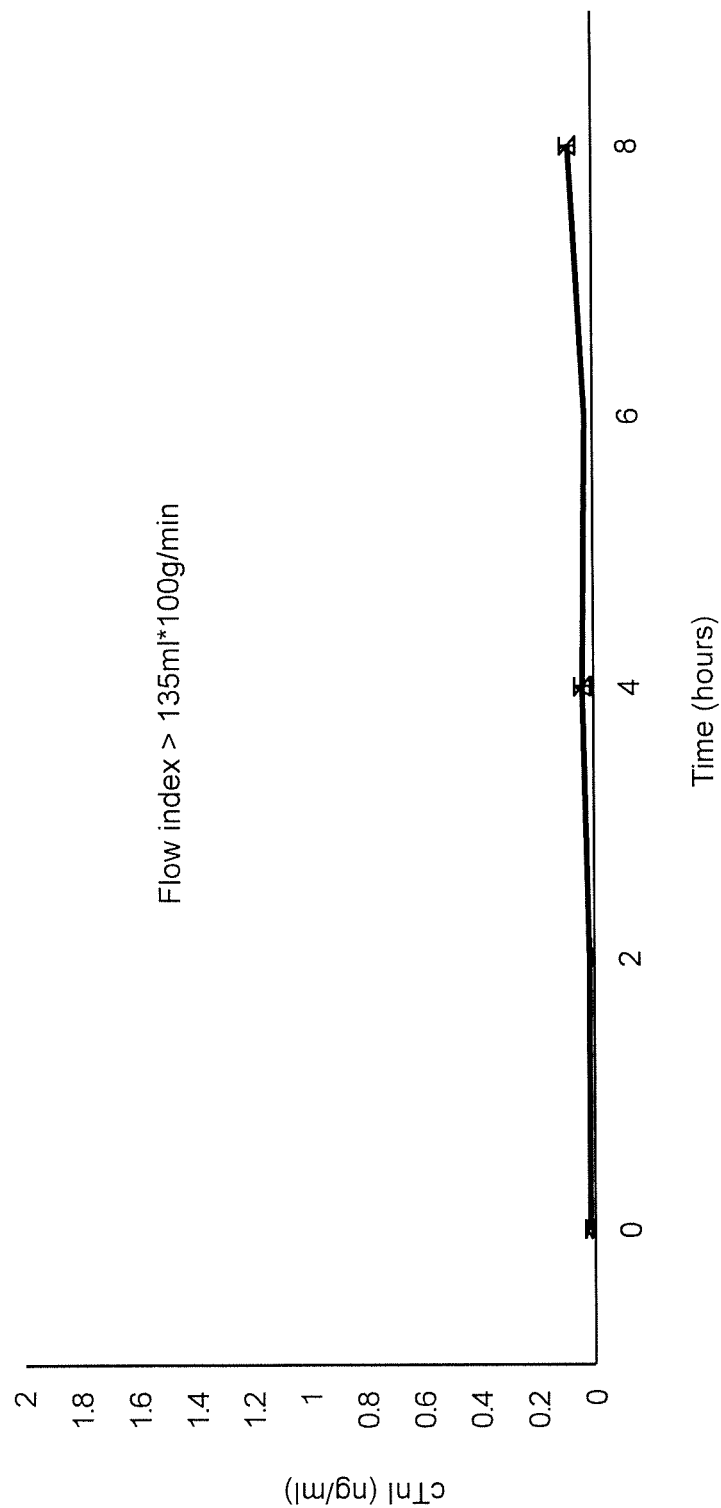
FIG. 17A-C. Cardiac troponin I (cTnI) was measured as a measure of cardiac injury in a set of 6 hearts perfused at constant flow above the $D_{crit}$ at 15° C. for 8 hours. A, low levels of cTNI were measured during the perfusion time without any statistically significant increase compared to the first baseline samples that were collected at time 0; B, the dotted line shows the values of cTnI measured after perfusion of the rat hearts using St. Thomas Solution II, which is used to induce cardioplegia and for static cold heart storage. Cellular damage develops over time, as reflected by the increase in cTnI during the first 3 hours of perfusion; C, the graph indicates the values of cTnI measured in samples collected from perfused hearts following a short or a long period of ischemia, and shows the ranges of values associated with cardiomyocyte damage and death.
Figure 17B:
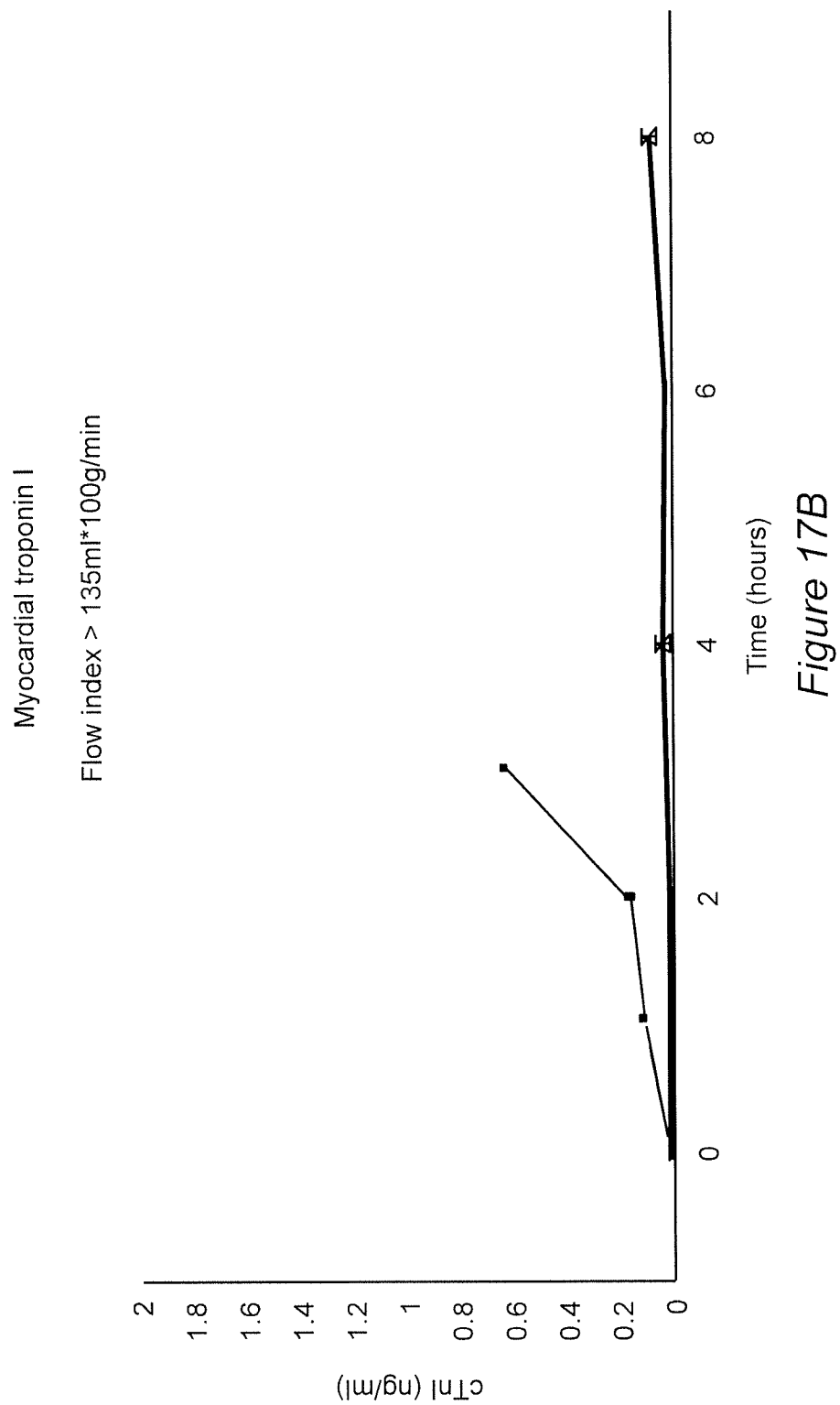
Figure 17C:
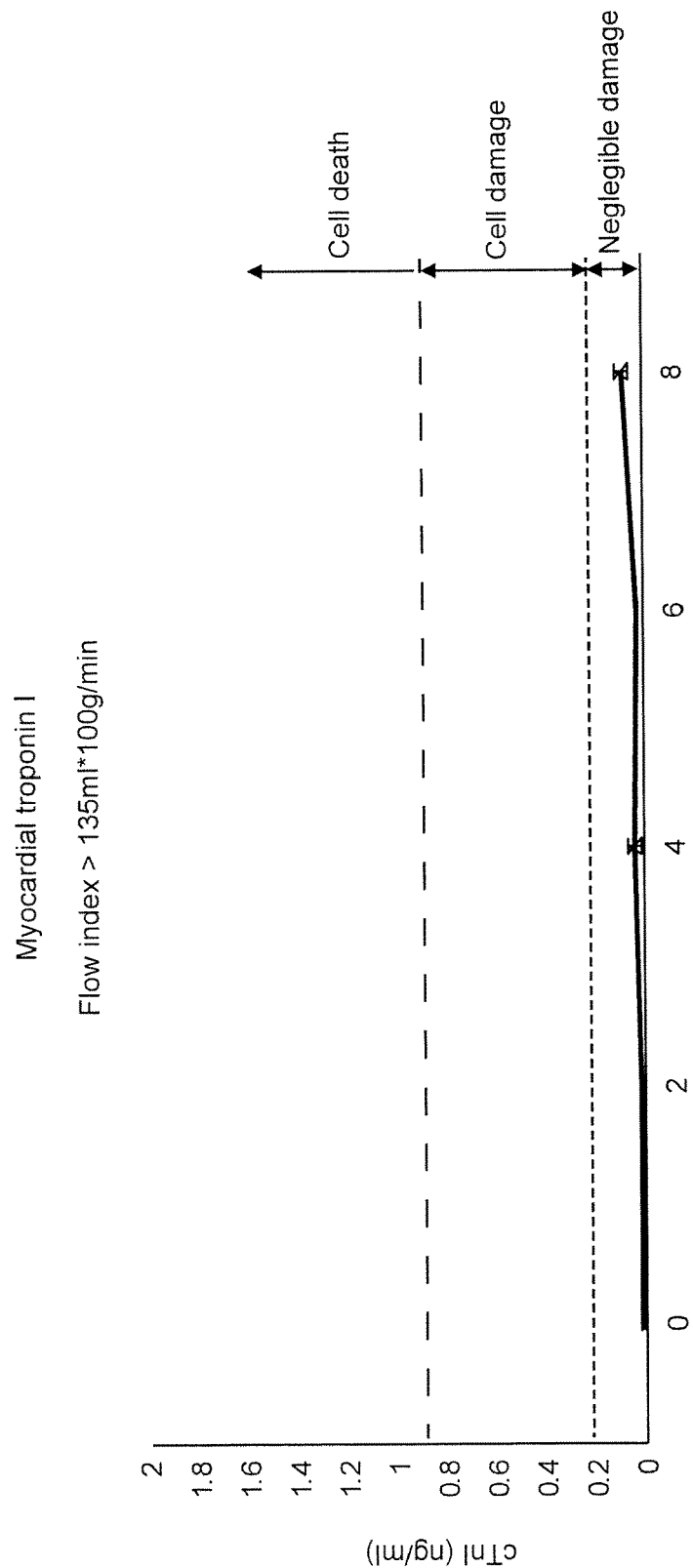

IVC eluate was collected at time 0, 2, 4, 6, 8 hours to determine the amount of cardiac troponin I (cTnI) released into the solution, as a marker of myocardial damage (FIG. 17A-C). Stable, low levels of cTnI were measured along the set experimental time, indicating low cellular damage and adequate tissue preservation.

Figure 16:
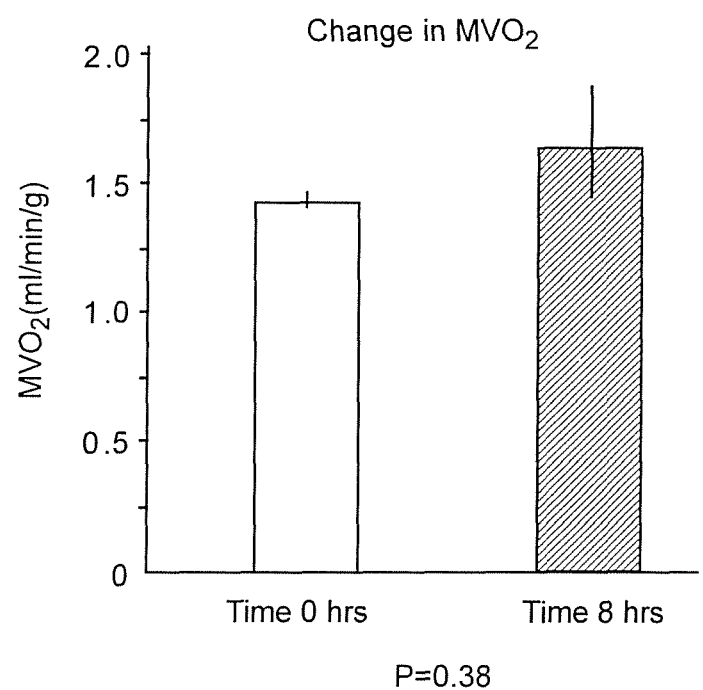
FIG. 16. $MVO_2$ was calculated for all the rat hearts perfused at time zero and at 8 hours and showed no decrease over this time period.

Discussion:

Ex-vivo perfusion of organs and tissues requires that the oxygen delivery, established by the product of the perfusate flow rate and the amount of oxygen being carried by each ml of perfusate, reach a critical point where the delivery ($DVO_2$) at least meets the demand of the tissue ($MVO_2$). This minimal oxygen delivery is called the critical delivery ($D_{CRIT}$) or minimal flow necessary under those conditions. This often is not determined in traditional organ perfusion preservation of kidneys because perfusion is performed at such profoundly hypothermic temperatures (2-4° C.) that the demand of the tissue is so low that adequate delivery is not questioned. However, organ and tissue reanimation requires warmer temperatures (mid-thermia, 15-22° C.) so the critical oxygen delivery point ($D_{CRIT}$) of a metabolically active tissue like myocardium needs to be determined to avoid underperfusion. FIG. 15 shows the $D_{CRIT}$ of the heart at 15° C. is equal to 108 ml/min/100 g tissue wt. All flows must be at this rate or higher to prevent tissue ischemia during the perfusion period. Only the substitution of PEG-20k for hydroxyethyl starch in MPS solution allowed us to be able to conduct this experiment because the tissue otherwise progressively becomes swollen, which caused secondary capillary compression that further reduced perfusate delivery in a self-amplifying cycle. In contrast, the new PEG-20k-containing solution gave remarkable stability to the preparation since the $MVO_2$ of the tissue remained steady from the start of perfusion until the end of perfusion 8 hours later (FIG. 16). Without being bound by theory, this likely means that PEG-20k impermeants added to the perfusate allowed for low pressure perfusion by preventing cell swelling and subsequent capillary compression. This increased capillary oxygen transfer enough to allow for steady $DVO_2$ under steady and low vascular resistance.

To determine if the tissue remained unharmed during the 8 hour perfusion period, which will be needed if hearts are to be transplanted, the time dependent release of myocardial specific markers of ischemic injury (troponin-1) into the perfusate was examined. This is the same marker used clinically to determine if a patient has had a heart attack. FIGS. 17A-C show troponin release into the perfusate over time. Very low levels over 8 hours were observed (FIG. 17A), which indicates healthy cardiac tissue with no ischemia. FIG. 17B shows the same troponin results with a superimposed graph of troponin release by hearts perfused with St. Thomas Solution, which is a common solution used to preserve hearts for cold storage transplantation. Finally, the electrical-mechanical activity of the hearts (organized heart beat and rhythm) were restarted after 8 hours of perfusion preservation, which further suggests fitness for transplantation.

In summary, the addition of the PEG-20k impermeant (in place of the native hydroxyethyl starch in UW-MPS) allowed for stable low pressure perfusion of heart at flow rates above the critical oxygen delivery ($D_{CRIT}$) values at each temperature tested, which defines non-ischemic perfusion. Vascular resistance, flow, and oxygen delivery remained stable over the perfusion period. Viability of tissue was verified by low to absent release of myocardial tissue troponin-1 enzyme release into the perfusion solution over 8-hours. Addition of PEG-20k impermeants increased the efficiency of capillary perfusion so much that $D_{CRIT}$ was achieved at both temperatures without the use or need for an oxygen carrier (such as hemoglobin). The new PEG-20k modified MPS solution is thus capable of preserving standard criteria donor hearts for 8 hours with minimal functional loss. In addition, the new PEG-20k modified MPS solution produces conditions favorable for reanimation of injured (DCD) donor hearts by allowing prolonged (8 hour) and stable perfusion conditions for drug treatment effects to occur.

These results indicate for the first time that prolonged, low pressure, low resistance, and high efficient ex-vivo machine perfusion of the myocardium is possible at mid-thermic temperatures by controlling cell and tissue volume and secondary capillary oxygen transport using the exemplary hybrid cell impermeant PEG-20k. Thus, donor hearts can be metabolically suspended at mid-thermia for at least 8 hours after recovery from the donor to either serve as a new and improved preservation method for standard criteria donor hearts, or for establishing a safe period for tissue metabolic and molecular repair of damaged donor hearts (reanimation) to expand the donor pool.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

1. National Center for Injury Prevention and Control. Web-based Injury Statistics Query and Reporting System (WISQARS). 2013. Ref Type: Online Source
2. Finkelstein E A, Corso P S, Miller T R. *The Incidence and Economic Burden of Injuries in the United States*. USA. Oxford University Press; 2006.
3. Kauvar D S, Lefering R, Wade C E. Impact of hemorrhage on trauma outcome: an overview of epidemiology, clinical presentations, and therapeutic considerations. *J Trauma*. 2006; 60:S3-11.
4. Heckbert S R, Vedder N B, Hoffman W, Winn R K, Hudson L D, Jurkovich G J, Copass M K, Harlan J M, Rice C L, Maier R V. Outcome after hemorrhagic shock in trauma patients. *J Trauma*. 1998; 45:545-549.
5. Franklin G A, Boaz P W, Spain D A, Lukan J K, Carrillo E H, Richardson J D. Prehospital hypotension as a valid indicator of trauma team activation. *J Trauma*. 2000; 48:1034-1037.
6. Riha G M, Kunio N R, Van P Y, Hamilton G J, Anderson R, Differding J A, Schreiber M A. Hextend and 7.5% hypertonic saline with Dextran are equivalent to Lactated Ringer's in a swine model of initial resuscitation of uncontrolled hemorrhagic shock. J Trauma. 2011; 71:1755-1760.
7. Riha G M, Kunio N R, Van P Y, Kremenevskiy I, Anderson R, Hamilton G J, Differding J A, Schreiber M A. Uncontrolled hemorrhagic shock results in a hypercoagulable state modulated by initial fluid resuscitation regimens. *J Trauma Acute Care Surg*. 2013; 75:129-134.
8. Holcomb J B, Pati S. Optimal trauma resuscitation with plasma as the primary resuscitative fluid: the surgeon's perspective. *Hematology Am Soc Hematol Educ Program*. 2013; 2013:656-659.
9. Chaudry I H, Sayeed M M, Baue A E. Depletion and restoration of tissue ATP in hemorrhagic shock. *Arch Surg*. 1974; 108:208-211.
10. Gomez H, Mesquida J, Hermus L et al. Physiologic responses to severe hemorrhagic shock and the genesis of cardiovascular collapse: can irreversibility be anticipated? *J Surg Res*. 2012; 178:358-369.
11. Chaudry I H. Use of ATP following shock and ischemia. *Ann NY Acad Sci*. 1990; 603:130-140.
12. Barlet-Bas C, Khadouri C, Marsy S, Doucet A. Enhanced intracellular sodium concentration in kidney cells recruits a latent pool of Na—K-ATPase whose size is modulated by corticosteroids. *J Biol Chem*. 1990; 265:7799-7803.
13. Petit P X, Goubern M, Diolez P, Susin S A, Zamzami N, Kroemer G. Disruption of the outer mitochondrial membrane as a result of large amplitude swelling: the impact of irreversible permeability transition. *FEBS Lett*. 1998; 426:111-116.
14. Southard J H, Belzer F O. Organ preservation. *Annu Rev Med*. 1995; 46:235-247.
15. Southard J H, Beltzer F O. Principles of Organ Preservation Part I. Surgical Rounds. 1993; 353-360.
16. Southard J H, Beltzer F O. Principles of Organ Preservation Part II. Surgical Rounds. 1993; 443-448.
17. Southard J H, Belzer F O. Control of canine kidney cortex slice volume and ion distribution at hypothermia by impermeable anions. *Cryobiology*. 1980; 17:540-548.
18. Southard J H, van Gulik T M, Ametani M S, Vreugdenhil P K, Lindell S L, Pienaar B L, Belzer F O. Important components of the U W solution. *Transplantation*. 1990; 49:251-257.
19. Mees N, Southard J H, Belzer F O. Inhibition of ischemic induced cellular swelling in kidney cortex tissue by lactobionate anions. *J Trauma*. 1982; 22:118-120.
20. Parrish, D., Lindell, S., Reichstetter, H., Aboutanos, M., and Mangino, M. J. Cell impermeant based low volume resuscitation in hemorrhagic shock: A biological basis for injury involving cell swelling. *Ann. Surg.* 2014. Ref Type: In Press
21. Arora T K, Malhotra A K, Ivatury R, Mangino M J. L-arginine infusion during resuscitation for hemorrhagic shock: impact and mechanism. *J Trauma Acute Care Surg.* 2012; 72:397-402.
22. Ionac M. One technique, two approaches, and results: thoracic duct cannulation in small laboratory animals. *Microsurgery.* 2003; 23:239-245.
23. Reed R K, Townsley M I, Taylor A E. Estimation of capillary reflection coefficients and unique P S products in dog paw. *Am J Physiol.* 1989; 257:H1037-H1041.
24. Mortillaro N A, Granger D N, Kvietys P R, Rutili G, Taylor A E. Effects of histamine and histamine antagonists on intestinal capillary permeability. *Am J Physiol.* 1981; 240:G381-G386.

What is claimed is:

1. A method for prolonging low volume resuscitation in a subject in need thereof, comprising the steps of:
    administering intravenously or intraosseously to said subject 2000 milliliters or less of an organ protectant solution comprising at least one polyethylene glycol (PEG) polymer with a molecular weight of 20,000 daltons present at a concentration of 7.5-10% by weight,
    wherein said PEG polymer increases oncotic pressure and causes water to transfer from interstitial space into vascular space reducing cell swelling and promoting microcirculatory blood flow for at least 2 hours in said subject administered with said organ protectant solution.

2. The method of claim 1, wherein the organ protectant solution further comprises one or more cell impermeant molecules present at a concentration of at least 10-60% by weight, wherein at least one of said one or more cell impermeant molecules can cross a capillary endothelium and preferentially load into an extracellular fluid compartment in said subject and increase a theoretical extracellular fluid osmolarity without entering one or more of endothelial and parenchymal cells.

3. The method of claim 2, wherein at least one of said one or more cell impermeant molecules is selected from the group consisting of sorbitol, gluconate, trehalose, raffinose, lactobionate, and maltitol.

4. The method of claim 3, wherein said at least one of said one or more cell impermeant molecules is gluconate.

5. The method of claim 1, wherein 100 ml to 500 ml of said organ protectant solution is administered in said administering step.

6. A method of treating severe hypotension in a subject comprising the step of:
    Administering to said subject intravenously or intraosseously no more than 2000 ml of a pharmaceutically acceptable organ protectant solution, comprising at least one polyethylene glycol (PEGA) polymer with a molecular weight of 20,000 daltons at a concentration of 7.5 to 10% by weight, in an amount sufficient to raise blood pressure to at least 35 mmHg in said subject and extend a time period for low volume resuscitation to at least 2 hours.

7. The method of claim 6, wherein the pharmaceutically acceptable organ protectant solution further comprises at least one impermeant molecule selected from the group of gluconate, raffinose and trehalose at a total concentration ranging from 10% to 35% by weight.

8. The method of claim 6, wherein 100-500 ml of said pharmaceutically acceptable organ protectant solution is administered as an intravenous drip solution.

* * * * *